(12) United States Patent
Danielsson et al.

(10) Patent No.: US 11,150,361 B2
(45) Date of Patent: *Oct. 19, 2021

(54) X-RAY IMAGING SYSTEM FOR PHASE CONTRAST IMAGING USING PHOTON-COUNTING EVENTS

(71) Applicant: Prismatic Sensors AB, Stockholm (SE)

(72) Inventors: Mats Danielsson, Täby (SE); Christel Sundberg, Stockholm (SE)

(73) Assignee: PRISMATIC SENSORS AB, Stockholm (SE)

( * ) Notice: Subject to any disclaimer, the term of this patent is extended or adjusted under 35 U.S.C. 154(b) by 112 days.

This patent is subject to a terminal disclaimer.

(21) Appl. No.: 16/653,191

(22) Filed: Oct. 15, 2019

(65) Prior Publication Data

US 2020/0158895 A1 May 21, 2020

Related U.S. Application Data

(60) Provisional application No. 62/769,099, filed on Nov. 19, 2018.

(51) Int. Cl.
  *G01T 1/24* (2006.01)
  *G01N 23/041* (2018.01)
  (Continued)

(52) U.S. Cl.
  CPC .............. *G01T 1/243* (2013.01); *A61B 6/032* (2013.01); *A61B 6/4241* (2013.01); *A61B 6/484* (2013.01);
  (Continued)

(58) Field of Classification Search
  CPC ...... G01T 1/243; G01N 23/041; A61B 6/032; A61B 6/4241; A61B 6/484
  See application file for complete search history.

(56) References Cited

U.S. PATENT DOCUMENTS

| | | |
|---|---|---|
| 8,183,535 B2 | 5/2012 | Danielsson et al. |
| 2002/0044628 A1 | 4/2002 | Hussein et al. |

(Continued)

FOREIGN PATENT DOCUMENTS

| | | |
|---|---|---|
| CN | 104569002 A | 4/2015 |
| CN | 105935297 A | 9/2016 |
| WO | 2014/100063 A1 | 6/2014 |

OTHER PUBLICATIONS

International Search Report and Written Opinion, dated Dec. 10, 2019, from corresponding PCT application No. PCT/SE2019/051010.

*Primary Examiner* — Hugh Maupin
(74) *Attorney, Agent, or Firm* — Nixon & Vanderhye

(57) ABSTRACT

An x-ray imaging system includes an x-ray source and detector. The detector is a photon counting x-ray detector, enabling detection of photon-counting events. The system acquires at least one phase contrast image based on photon-counting events. The detector includes x-ray detector sub-modules, also referred to as wafers, each including detector elements. The sub-modules are oriented in edge-on geometry with their edge directed towards the x-ray source, assuming the x-rays enter through the edge. Each sub-module or wafer has a thickness with two opposite sides of different potentials to enable charge drift towards the side, where the detector elements/pixels, are arranged. The system estimates charge diffusion from a Compton interaction or an interaction through photoeffect related to an incident x-ray photon in a sub-module or wafer of the x-ray detector, and estimates a point of interaction of the x-ray photon sub-module based on the determined estimate of charge diffusion.

29 Claims, 20 Drawing Sheets

(51) Int. Cl.
*G01N 23/083* (2018.01)
*A61B 6/00* (2006.01)
*H04N 5/32* (2006.01)
*A61B 6/03* (2006.01)

(52) U.S. Cl.
CPC ......... *A61B 6/5235* (2013.01); *G01N 23/041* (2018.02); *G01N 23/083* (2013.01); *G01T 1/244* (2013.01); *H04N 5/32* (2013.01); *G01N 2223/401* (2013.01); *G01N 2223/413* (2013.01)

(56) References Cited

U.S. PATENT DOCUMENTS

| | | |
|---|---|---|
| 2008/0103391 A1* | 5/2008 | Dos Santos Varela ........................ A61B 6/037 600/436 |
| 2010/0204942 A1 | 8/2010 | Danielsson et al. |
| 2012/0033785 A1* | 2/2012 | Michel .................. A61B 6/484 378/21 |
| 2013/0028379 A1 | 1/2013 | Nelson et al. |
| 2013/0032715 A1 | 2/2013 | Zhu et al. |
| 2014/0270070 A1 | 9/2014 | Spahn |
| 2016/0163072 A1 | 6/2016 | Koehler et al. |
| 2016/0217596 A1 | 7/2016 | Koehler et al. |
| 2016/0324496 A1 | 11/2016 | Fredenberg et al. |
| 2017/0206682 A1 | 7/2017 | Roessl et al. |
| 2017/0219503 A1 | 8/2017 | Vedantham et al. |
| 2018/0188190 A1* | 7/2018 | Durko .............. G01N 23/20075 |
| 2020/0158663 A1* | 5/2020 | Danielsson ............. G01T 1/241 |

* cited by examiner

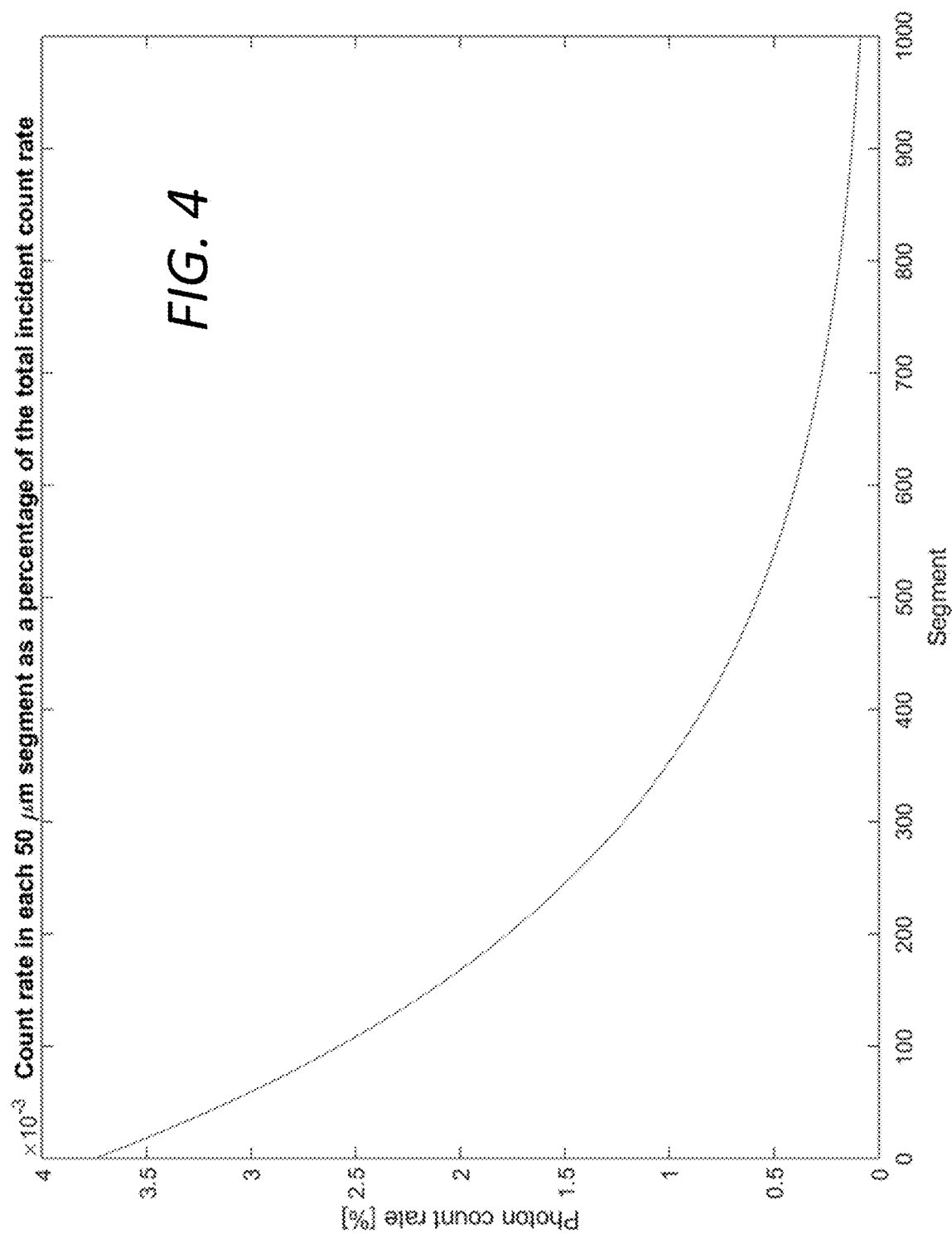

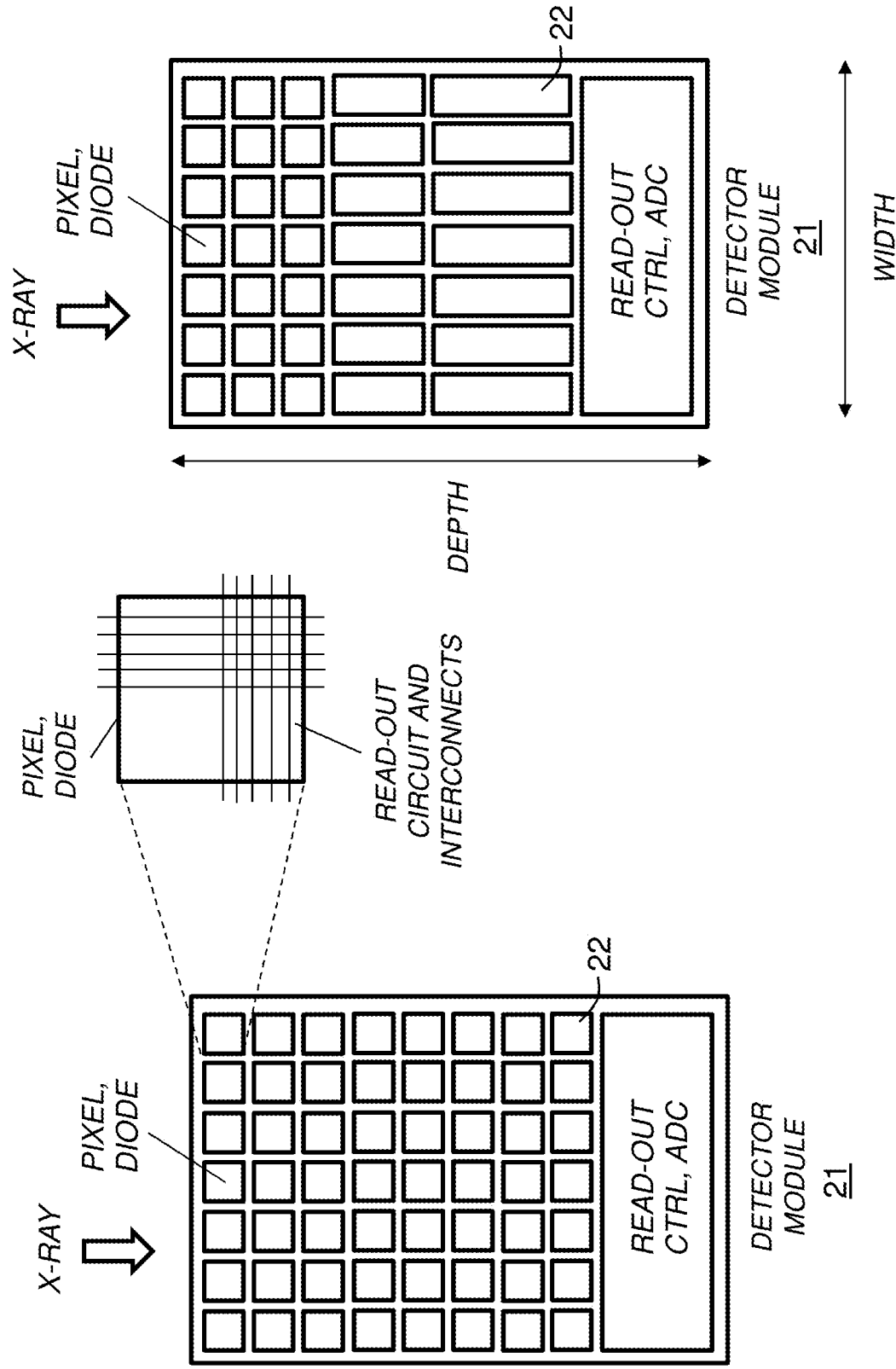

X-RAY IMAGING SYSTEM FOR PHASE CONTRAST IMAGING USING PHOTON-COUNTING EVENTS

The project leading to this application has received funding from the European Union's Horizon 2020 research and innovation programme under grant agreement No 830294.

TECHNICAL FIELD

The proposed technology relates to x-ray imaging, and more particularly to an x-ray imaging system and a phase contrast x-ray imaging system.

BACKGROUND

Radiographic imaging such as x-ray imaging has been used for years in medical applications and for non-destructive testing.

Normally, an x-ray imaging system includes an x-ray source and an x-ray detector system. The x-ray source emits x-rays, which pass through a subject or object to be imaged and are then registered by the x-ray detector system. Since some materials absorb a larger fraction of the x-rays than others, an image is formed of the subject or object.

It may be useful to begin with a brief overview of an illustrative overall x-ray imaging system, with reference to FIG. 1. In this non-limiting example, the x-ray imaging system 100 basically comprises an x-ray source 10, an x-ray detector system 20 and an associated image processing device 30. In general, the x-ray detector system 20 is configured for registering radiation from the x-ray source 10 that may have been focused by optional x-ray optics and passed an object or subject or part thereof. The x-ray detector system 20 is connectable to the image processing device 30 via suitable analog processing and read-out electronics (which may be integrated in the x-ray detector system 20) to enable image processing and/or image reconstruction by the image processing device 30.

Phase contrast imaging is a relatively new and different concept to x-ray imaging as we know it today and has shown great promise delivering high contrast images. There have been various technical solutions suggested over the last years but they have all been impractical and none has reached the clinic.

FIG. 2 is a schematic diagram illustrating an example of an X-ray grating interferometer.

The most promising approach uses i) a source grating G0 at the x-ray source to improve coherence and ii) a phase shift grating G1, placed after the object, that acts as a beam splitter and generates an interference pattern that can be analyzed with iii) an analyzer absorption grating G2. The signal is obtained by scanning G1 or G2 along the transverse direction x. More information on the general setup of x-ray grating interferometer can be found, e.g. in reference [1].

The scanning takes time and increases radiation dose which is very undesirable in all clinical applications. The G2 grating also absorbs part of the radiation, and therefore a higher radiation dose may have to be used. If the detector has sufficiently high spatial resolution, of the order of 1-5 um, the last grating is not needed, so called G2-less grating interferometry [2]. The x-ray will create an electron when interacting with the sensor and the electron in turn will create an electron hole cloud that will be detected in the sensor pixels. The charge cloud is normally larger than the pixel size but by processing the signal from each pixel and considering the charge sharing a spatial resolution an order of magnitude higher than the pixel size can be achieved, for example with weighted average techniques [3]. The problem with this method is that it is prone to so-called pile-up if several x-rays interact close to each other and is therefore restricted to very low fluxes. In all clinical applications, however, the flux is high in order to obtain the image in a short time to avoid motion artefacts.

Reference [5] relates to a method and apparatus for enhanced Phase Contrast Imaging (PCI) and dual-use radiation imaging systems. In one implementation, high resolution storage phosphor plate radiation detector (an area detector) is employed for conventional attenuation radiation imaging and/or PCI including conventional PCI and coded aperture PCI.

Reference [6] relates to a method and apparatus for obtaining a phase-contrast digital radiographic imaging system and methods for same that can include an x-ray source for radiographic imaging; a beam shaping assembly including a collimator and a source grating, an x-ray grating interferometer including a phase grating, and an analyzer grating; and an x-ray detector, where a single arrangement of the beam shaping assembly, the x-ray grating interferometer and a position of the detector is configured to provide spectral information (e.g. at least two images obtained at different relative beam energies).

Reference [7] relates to an x-ray phase contrast imaging apparatus and method of operating the same. The apparatus passes x-rays generated by an x-ray source through, in succession, a source grating, an object of interest, a phase grating, and an analyzer grating. The x-ray source, the source grating, the phase grating, and the analyzer grating move as a single entity relative to an object of interest. The phase grating and the analyzer grating remain in fixed relative location and fixed relative orientation with respect to one another. The detected x-rays are converted to a time sequence of electrical signals.

Reference [8] relates to an x-ray imaging system includes an x-ray source, an x-ray detector including a plurality of detector strips arranged in a first direction of the x-ray detector. Each detector strip includes a plurality of detector pixels arranged in a second direction of the x-ray detector. A phase grating and a plurality of analyzer gratings including grating slits are disposed between the x-ray source and detectors. The x-ray source and the x-ray detector are adapted to perform a scanning movement in relation to an object in the first direction, in order to scan the object. Each of the plurality of analyzer gratings is arranged in association with a respective detector strip with the grating slits arranged in the second direction. The grating slits of the analyzer gratings of the detector strips are offset relative to each other in the second direction.

Reference [9] relates to an x-ray recording system is for differential phase contrast imaging of an examination object via phase stepping. In an embodiment, the x-ray recording system includes at least one x-ray emitter for generating quasi coherent x-ray radiation; an x-ray image detector with pixels arranged in a matrix; a defraction or phase grating arranged between the examination object and the x-ray image detector; and an analyzer grating assigned to the phase grating, wherein x-ray emitter, x-ray image detector, phase grating and analyzer grating for the phase contrast imaging form components in an arrangement.

Reference [10] relates to an x-ray phase contrast imaging system based on photon counting and also discloses an x-ray phase contrast imaging method realized by the system and key equipment of the x-ray phase contrast imaging method.

Reference [11] relates to an X-ray grating phase-contrast imaging CT system. The X-ray grating phase-contrast imaging CT system comprises an X-ray light source, a source grating, a beam splitting grating, an analysis grating and a detector which are arranged in sequence, wherein the X-ray light source and the source grating are relatively and fixedly integrated to form a first module, the analysis grating and the detector are relatively and fixedly integrated to form a second module, the first module, the beam splitting grating and the second module rotate around a sample table between the beam splitting grating and the analysis grating, and a stereoscopic image is obtained through scanning.

SUMMARY

It is a general object to provide improvements related to x-ray imaging.

It is also desirable to enable phase contrast imaging in clinical solutions.

It is a specific object to provide an x-ray imaging system.

According to an aspect, there is provided an x-ray imaging system comprising an x-ray source, and an associated x-ray detector. The x-ray detector is a photon counting x-ray detector for enabling detection of photon-counting events.

The overall x-ray imaging system is configured for enabling acquisition of at least one phase contrast image based on detected photon-counting events.

The x-ray detector is based on a number of x-ray detector sub-modules, also referred to as wafers, each of which comprises detector elements. The x-ray detector sub-modules are oriented in edge-on geometry with their edge directed towards the x-ray source, assuming the x-rays enter through the edge. Each x-ray detector sub-module or wafer has a thickness with two opposite sides of different potentials to enable charge drift towards the side, where the detector elements, also referred to as pixels, are arranged.

The x-ray imaging system is configured to determine an estimate or measure of charge diffusion originating from a Compton interaction or an interaction through photoeffect related to an incident x-ray photon in an x-ray detector sub-module or wafer of the x-ray detector, and to determine an estimate of the point of interaction of the incident x-ray photon in the x-ray detector sub-module based on the determined estimate or measure of charge diffusion.

Expressed slightly differently, the x-ray imaging system is configured for using the determined estimate of charge diffusion to provide a significantly improved estimate of the point of interaction of the incident x-ray photon in the detector sub-module.

In other words, information about the charge cloud or the charge diffusion may be used to improve the resolution in one or several directions of a sub-detector module or wafer of an x-ray detector.

In this way, the proposed technology will enable phase contrast imaging into a feasible clinical solution, for example for Computed Tomography (CT) imaging. The resolution is significantly improved, and the proposed technology allows new imaging procedures to be accomplished.

BRIEF DESCRIPTION OF DRAWINGS

FIG. 4 is a schematic diagram illustrating an example of the photon count rate as a function of segment in a depth-segmented x-ray detector.

FIG. 7 is a schematic diagram illustrating an example of an x-ray detector sub-module according to an embodiment.

FIG. 8 is a schematic diagram illustrating another example of an x-ray detector sub-module according to an embodiment.

DETAILED DESCRIPTION

Figure 1:
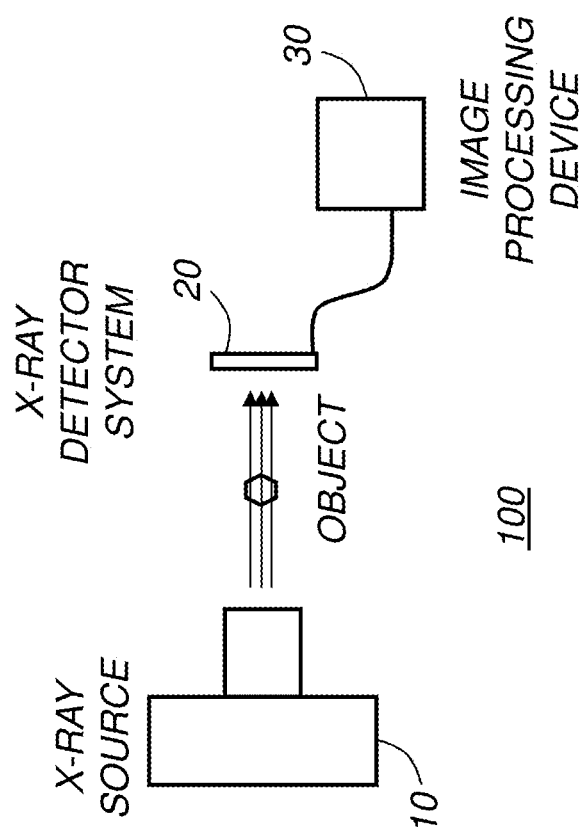
FIG. 1 is a schematic diagram illustrating an example of an overall x-ray imaging system.
Figure 2:
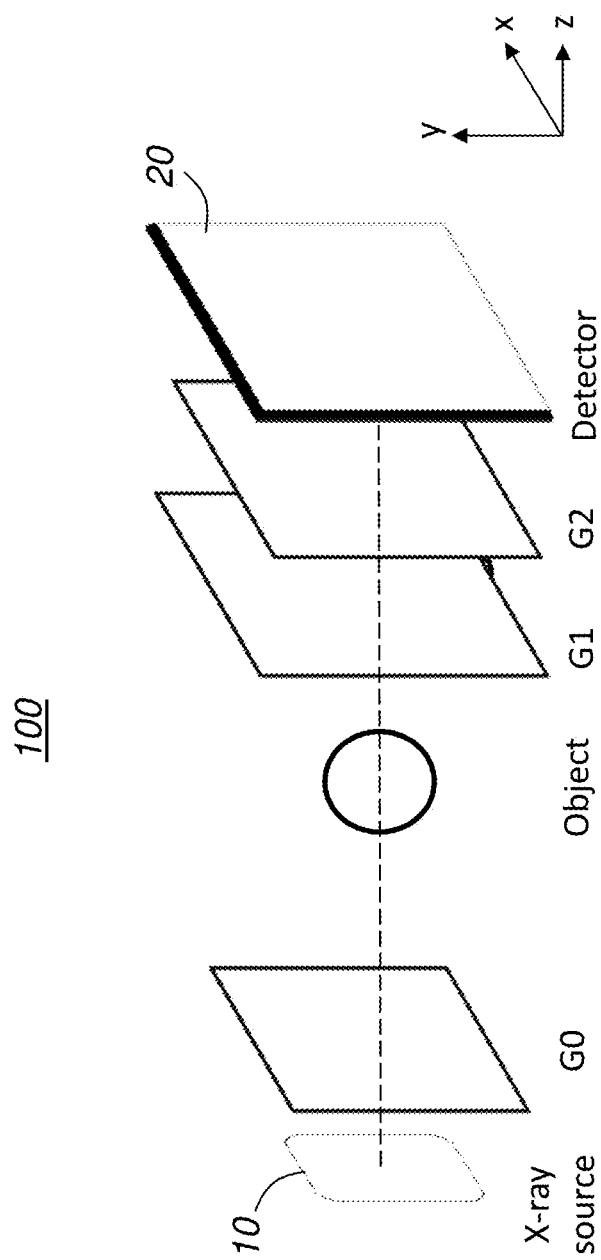
FIG. 2 is a schematic diagram illustrating an example of an X-ray grating interferometer.

We suggest a new solution that will enable phase contrast imaging into a feasible clinical solution, for example for CT imaging.

According to an aspect, there is provided an x-ray imaging system comprising an x-ray source, and an associated x-ray detector. The x-ray detector is a photon counting x-ray detector for enabling detection of photon-counting events.

The overall x-ray imaging system is configured for enabling acquisition of at least one phase contrast image based on detected photon-counting events.

The x-ray detector is based on a number of x-ray detector sub-modules or wafers, each of which comprises detector elements. The x-ray detector sub-modules are oriented in edge-on geometry with their edge directed towards the x-ray source, assuming the x-rays enter through the edge. Each detector sub-module or wafer has a thickness with two opposite sides of different potentials to enable charge drift towards the side (typically the front side), where the detector elements, also referred to as pixels, are arranged.

The x-ray imaging system is configured to determine an estimate or measure of charge diffusion originating from a Compton interaction or an interaction through photoeffect related to an incident x-ray photon in an x-ray detector sub-module or wafer of the x-ray detector, and to determine an estimate of the point of interaction of the incident x-ray photon in the detector sub-module based on the determined estimate or measure of charge diffusion.

Normally, the interaction is an interaction between the x-ray photon and the semiconductor substrate (typically made of silicon).

In other words, information about the charge cloud or the charge diffusion may be used to improve the resolution in one or several directions of a sub-detector module or wafer of an x-ray detector.

As mentioned, the x-ray detector sub-modules are oriented in edge-on geometry with their edge directed towards the x-ray source, assuming the x-rays enter through the edge.

By way of example, the x-ray imaging system may be configured for enabling acquisition of said at least one phase contrast image based at least partly on detected Compton events. It is envisaged that it is easier to achieve very high resolution with Compton interactions, since a Compton electron travels a shorter distance compared to a photo electron since more energy is transferred in the latter case.

It should though be understood that if a high Z material is used in the detector, all interactions will be through photoeffect.

In a particular example, it may be useful to provide the x-ray imaging system with a phase shift grating located between the object or subject to be imaged and the x-ray detector for enabling acquisition of said at least one phase contrast image. For example, this could be a so-called G1 grating.

Normally, it is not necessary to use any analyzer absorption grating G2. A source grating G0 may optionally be used to improve coherence. However, it should be understood that with so-called micro focal x-ray technology (using a micro-focus x-ray source), the need for gratings may be avoided entirely, while still enabling phase contrast imaging.

As an example, each of the x-ray detector sub-modules may comprise detector elements distributed over the detector sub-module or wafer in two directions, including the direction of the incoming x-rays. This normally corresponds to a so-called depth-segmented x-ray detector sub-module. The proposed technology is however also applicable for use with non-depth-segmented x-ray detector sub-modules. The detector elements may be arranged as an array in a direction substantially orthogonal to the direction of the incident x-rays, while each of the detector elements is oriented edge-on to the incident x-rays. In other words, the x-ray detector sub-module may be non-depth-segmented, while still arranged edge-on to the incoming x-rays.

In a particular example, at least part of the detector elements, or pixels, have a longer extension in a direction of the incident X-rays than in a direction orthogonal to the direction of the incident X-rays, with a relation of at least 2:1. In other words, the detector elements, or pixels, may be asymmetric in the geometrical design and have at least double the extension (depth) in the direction of the incident X-rays than the extension in a direction orthogonal (perpendicular) to the direction of the incident X-rays.

By way of example, it is possible to have a design in which an estimate of charge diffusion can be determined in each of a number of particular detector sub-modules or wafers, and wherein an estimate of the point of interaction of the incident x-ray photon in the corresponding or respective detector sub-module can be determined. This can also be performed for each of a number of incident x-ray photons.

In other words, the x-ray imaging system may be configured to determine, for each of a number of incident x-ray photons and/or each of a number of x-ray detector sub-modules, a corresponding estimate of charge diffusion originating from a Compton interaction or an interaction through photoeffect related to the incident x-ray photon in the x-ray detector sub-module, and to determine an estimate of the point of interaction of the incident x-ray photon in the respective x-ray detector sub-module.

In this way, the proposed technology will enable phase contrast imaging into a feasible clinical solution, for example for CT imaging. The resolution is significantly improved, and allows new imaging procedures to be accomplished. Accordingly, the x-ray imaging system may be configured to enable phase contrast imaging for Computed Tomography.

In a particular embodiment, there is thus provided a phase contrast x-ray imaging system.

It should be understood that the x-ray imaging system may be configured to determine the estimate or measure of charge diffusion based on induced current caused by moving electron-hole pairs originating from the Compton interaction or interaction through photoeffect, as detected (i.e. the induced current) by detector elements distributed over the x-ray detector sub-module or wafer.

The charge diffusion may be represented by a charge cloud, and the estimate of charge diffusion may be represented by the width of the charge cloud, a location in which the highest charge of the charge cloud is detected and/or a position of the peak of the charge cloud, as detected by the detector elements distributed over the x-ray detector sub-module or wafer.

Preferably, the pixels are generally smaller than the charge cloud to be resolved. For example, the charge cloud may have a width in the order of 100 um, and the pixels are therefore normally designed to be smaller or even considerably smaller than that.

According to a particular aspect, information about the charge diffusion may be used for providing improved resolution in at least one of the two directions over which the detector elements are distributed on the main side of the detector sub-module or wafer. For example, increased resolution may be obtained based on information of a charge cloud profile in one or both of these directions. The considered direction(s) may include the length (x) direction and/or depth (z) direction of the detector sub-module or wafer.

It may also be desirable, as an alternative or a complement, to estimate the initial point of interaction along the thickness (y) of the detector sub-module based at least partly on the determined estimate of charge diffusion.

Accordingly, it has been shown that information about charge diffusion may be used to improve the resolution of the point of interaction of an incident x-ray photon in at least one of three directions (x, y, z) of an x-ray sub-detector module or wafer of an x-ray detector.

In a particular design example, each x-ray detector sub-module or wafer has detector elements distributed over the detector sub-module or wafer in two directions including i) the width/length direction (x) and ii) the depth direction (z) corresponding to the direction of the incoming x-rays, and the thickness (y) of the x-ray detector sub-module or wafer extends between the two opposite sides (such as back side and front side) of the x-ray detector sub-module.

By way of example, the x-ray imaging system may be configured to determine, at least partly based on the determined estimate of charge diffusion, the estimate of the point of interaction of the incident x-ray photon in at least one of the three directions (x, y, z) of an x-ray detector sub-module or wafer.

More particularly, the x-ray imaging system may be configured to determine, at least partly based on the determined estimate of charge diffusion, the estimate of the point of interaction of the incident x-ray photon in at least one of the two directions (x, z) over which the detector elements are distributed on a main side of the x-ray detector sub-module or wafer, and/or along the thickness (y) of the x-ray detector sub-module.

For example, the x-ray imaging system may be configured to determine, at least partly based on the determined estimate of charge diffusion, the estimate of the point of interaction of the incident x-ray photon based on information of a charge cloud profile in one or both of the two directions (x, z) over which the detector elements are distributed on a main side of the x-ray detector sub-module or wafer.

In a particular example, the x-ray imaging system may be configured for determining the charge cloud profile, performing curve fitting and finding out where the curve has its peak and identifying the peak as the point of interaction in a particular direction. This may provide sub-pixel resolution, which is highly beneficial.

Alternatively, the x-ray imaging system may be configured to determine the estimate of the point of interaction of the incident x-ray photon by identifying the pixel that has detected the highest charge (of the charge cloud) as the point of interaction.

In a particular example, the x-ray imaging system may be configured to estimate the initial point of interaction of the incident x-ray photon along the thickness (y) of the x-ray detector sub-module based at least partly on the determined estimate of charge diffusion.

As an example, the x-ray imaging system may be configured to measure or estimate the shape and/or width of the charge diffusion.

For example, the charge diffusion may be represented by a charge cloud, and the x-ray imaging system is configured to estimate the initial point of interaction of the incident x-ray photon along the thickness (y) of the x-ray detector sub-module based on the measured width of the cloud and the integrated charge of the cloud. A representation of the charge cloud may be provided by the induced current on triggered detector elements of a detector sub-module.

As the estimate of charge diffusion may be represented by the induced current, as detected by detector elements, the shape and/or width of the charge cloud may hence be related to the measured or detected induced current.

Optionally, the x-ray imaging system may be configured to determine an estimate of a distance, along the thickness of the x-ray detector sub-module, between a point of detection of the x-ray photon in the x-ray detector sub-module and the initial point of interaction based on the estimate of charge diffusion, and determine the estimate of the initial point of interaction based on the point of detection and the determined estimate of a distance along the thickness of the detector sub-module.

In a particular example, the detector elements distributed over the x-ray detector sub-module or wafer on the front side provide an array of pixels, where the pixels are smaller than the charge cloud to be resolved.

By way of example, at least one of the x-ray detector sub-modules may include a semiconductor substrate or material that comprises a plurality of active integrated pixels arranged in the semiconductor substrate. Preferably, the x-ray detector sub-module allows multiple active integrated pixels in the x-ray detector sub-module to detect a charge cloud generated by a single x-ray photon.

Optionally, all or part of the analog signal processing is integrated into the active integrated pixels.

For example, the active integrated pixels may be implemented as active integrated Complementary Metal Oxide Semiconductor (CMOS) pixels in the semiconductor substrate.

The x-ray detector is preferably a depth-segmented x-ray detector having two or more depth segments of detector elements in the direction of the incoming x-rays, where the depth of the x-ray detector ensures sufficient dose efficiency and the segmentation protects from so-called pulse pile-up.

Preferably, the x-ray imaging system is configured for G2-less phase contrast imaging, without using any analyzer absorption grating.

It is also possible to simultaneously acquire x-ray absorption and phase contrast images. In a particular example, the x-ray imaging system may be configured for enabling detection of photon-counting events and acquisition of at least one x-ray absorption image of an object or subject to be imaged based on the detected events. As mentioned, the overall x-ray imaging system comprises a phase shift grating located between the object or subject to be imaged and the x-ray detector system for enabling acquisition of at least one phase contrast image based on at least part of the detected photon-counting events, including Compton events. The overall x-ray imaging system may therefore be configured to simultaneously acquire at least one x-ray absorption image and at least one phase contrast image based on detected events.

For example, information of both x-ray absorption and phase contrast images may be combined in the image reconstruction process. In other words, it is possible to combine phase information as well as absorption information in the image reconstruction process, e.g. weighting the information. to provide a suitably merged image representation.

Expressed slightly differently, the x-ray imaging system may be configured to combine information of both x-ray absorption and phase contrast images in the image reconstruction process.

For example, the x-ray imaging system may be configured to combine phase information as well as absorption information in the image reconstruction process to provide a merged image representation.

It should also be understood that it is possible to use or operate only one of the absorption and phase contrast imaging modalities in the image reconstruction process.

In a particular example, the x-ray imaging system further comprises an associated image processing device connected to the x-ray detector system for performing image processing and/or image reconstruction.

Typically, the x-ray interactions will be distributed and occurring in different depth segments along the depth of the x-ray detector.

It should be understood that the depth of the x-ray detector is vital for dose efficiency and the segmentation protects from pulse pile-up and maintains the spatial resolution of the system.

In general, x-ray photons are converted to electron-hole pairs inside the semiconductor material of the x-ray detector, where the number of electron-hole pairs is generally proportional to the photon energy. The electrons and holes are drifting towards the detector elements, then leaving the photon-counting detector. During this drift, the electrons and holes induce an electrical current in the detector elements.

By way of example, the depth-segmented x-ray detector may include a plurality of x-ray detector sub-modules, each of which has a number of depth segments of detector elements in the direction of the incoming x-rays.

For example, the x-ray detector sub-modules may be arranged one after the other and/or arranged side-by-side in a configuration to form an effective detector area or volume.

Optionally, an anti-scatter module (such as an anti-scatter foil) may be integrated between at least some of the x-ray detector sub-modules.

By way of example, each x-ray detector sub-module is preferably connected to integrated circuitry for registration of x-rays interacting in the x-ray detector sub-module.

Figure 3A:
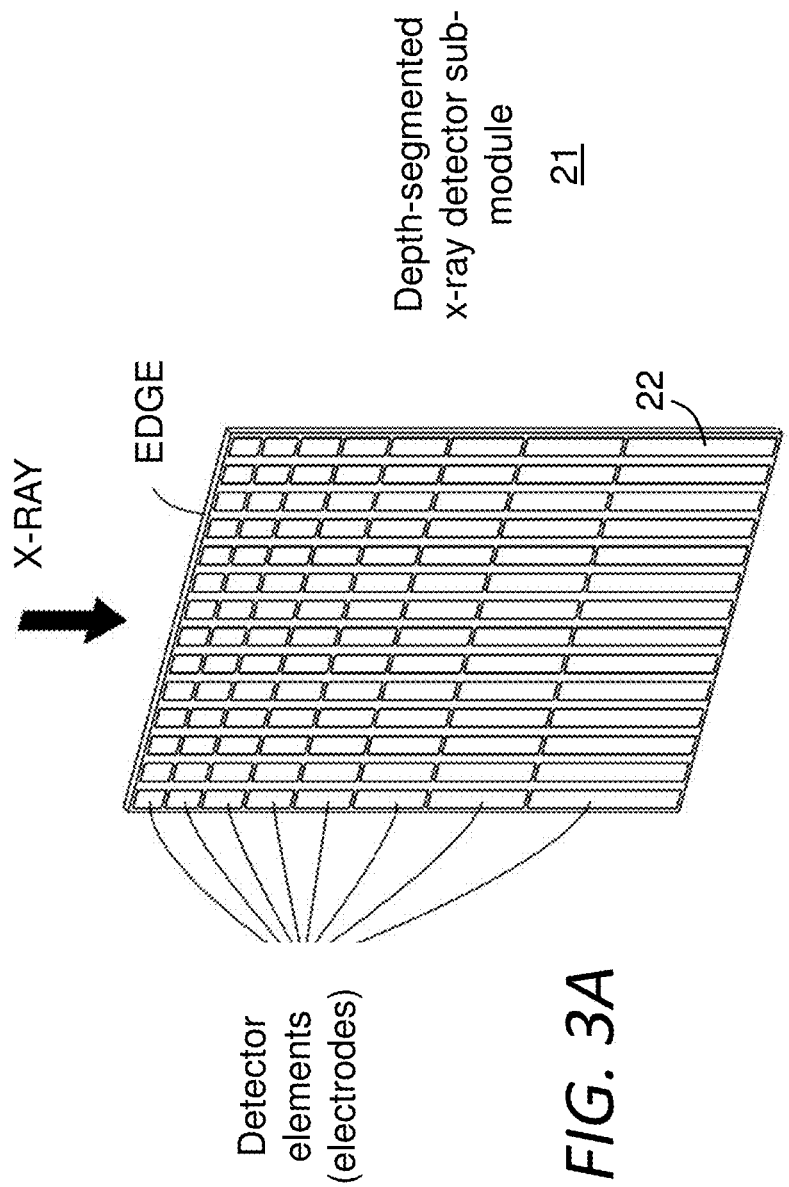
FIG. 3A is a schematic diagram illustrating an example of an x-ray detector sub-module according to an exemplary embodiment.

FIG. 3A is a schematic diagram illustrating an example of an x-ray detector sub-module according to an exemplary embodiment. In this example, the sensor part of the x-ray detector sub-module 21 is divided into so-called depth segments in the depth direction, assuming the x-rays enter through the edge. Each detector element 22 is normally based on a diode having a charge collecting electrode as a key component.

Normally, a detector element is an individual x-ray sensitive sub-element of the detector. In general, the photon interaction takes place in a (one or more) detector element and the thus generated charge is collected by the corresponding electrode of the detector element. Each detector element typically measures the incident x-ray flux as a sequence of frames. A frame is the measured data during a specified time interval, called frame time.

Figure 3B:
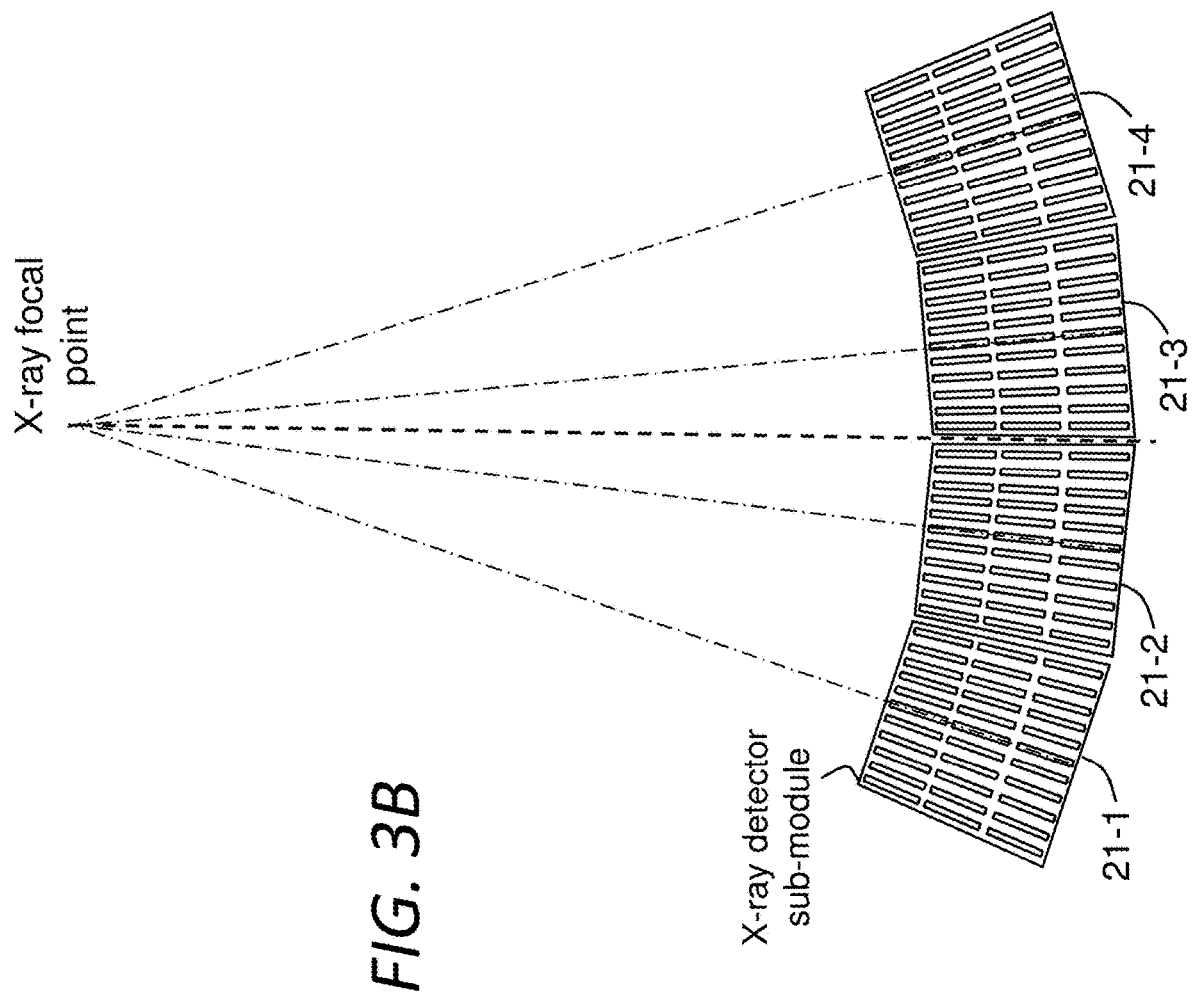
FIG. 3B is a schematic diagram illustrating an example of a modular x-ray detector comprising a number of detector sub-modules arranged side-by-side, e.g. in a slightly curved overall geometry with respect to an x-ray source located at an x-ray focal point.

FIG. 3B is a schematic diagram illustrating an example of a modular x-ray detector 20 comprising a number of detector sub-modules 21 arranged side-by-side, e.g. in a slightly curved overall geometry with respect to an x-ray source located at an x-ray focal point.

Figure 3C:
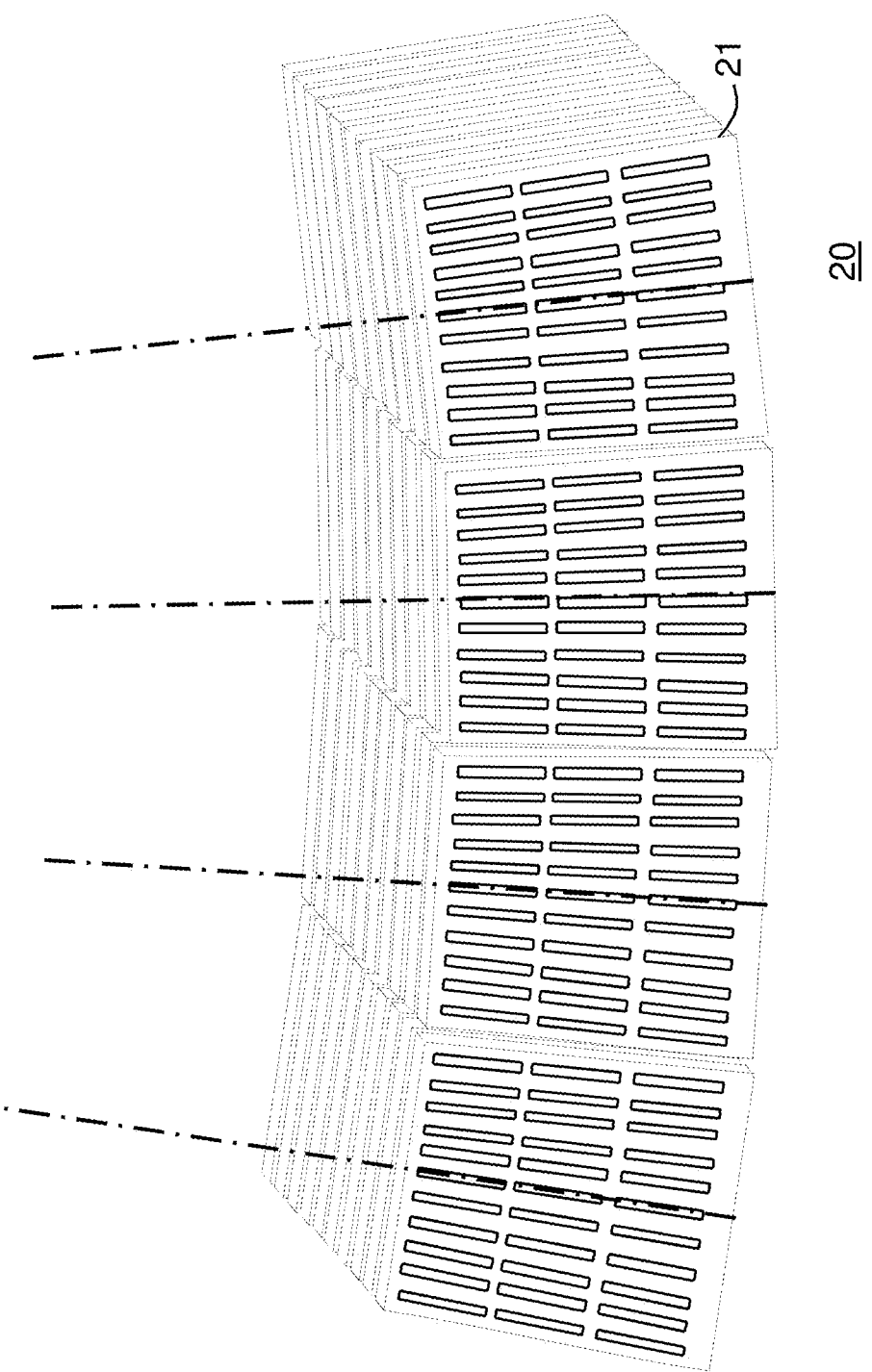
FIG. 3C is a schematic diagram illustrating an example of a modular x-ray detector comprising a number of detector sub-modules arranged side-by-side, and also stacked one after the other.

FIG. 3C is a schematic diagram illustrating an example of a modular x-ray detector 20 comprising a number of detector sub-modules 21 arranged side-by-side, and also stacked one after the other. The x-ray detector sub-modules 21 may be stacked one after the other to form larger detector modules that may be assembled together side-by-side to build up an overall x-ray detector system 20.

Edge-on is a design for an x-ray detector, where the x-ray sensors such as x-ray detector elements or pixels are oriented edge-on to incoming x-rays.

For example, the detector may have detector elements in at least two directions, wherein one of the directions of the edge-on detector has a component in the direction of the x-rays. Such an edge-on detector is sometimes referred to as a depth-segmented x-ray detector, having two or more depth segments of detector elements in the direction of the incoming x-rays.

Alternatively, the x-ray detector may be non-depth-segmented, while still arranged edge-on to the incoming x-rays.

Depending on the detector topology, a detector element may correspond to a pixel, e.g. when the detector is a flat-panel detector. However, a depth-segmented detector may be regarded as having a number of detector strips, each strip having a number of depth segments. For such a depth-segmented detector, each depth segment may be regarded as an individual detector element, especially if each of the depth segments is associated with its own individual charge collecting electrode.

The detector strips of a depth-segmented detector normally correspond to the pixels of an ordinary flat-panel detector. However, it is also possible to regard a depth-segmented detector as a three-dimensional pixel array, where each pixel (sometimes referred to as a voxel) corresponds to an individual depth segment/detector element.

Photon counting detectors have emerged as a feasible alternative in some applications; currently those detectors are commercially available mainly in mammography. The photon counting detectors have an advantage since in principle the energy for each x-ray can be measured which yields additional information about the composition of the object. This information can be used to increase the image quality and/or to decrease the radiation dose.

Compared to the energy-integrating systems, photon-counting CT has the following advantages. Firstly, electronic noise that is integrated into the signal by the energy-integrating detectors can be rejected by setting the lowest energy threshold above the noise floor in the photon-counting detectors. Secondly, energy information can be extracted by the detector, which allows improving contrast-to-noise ratio by optimal energy weighting and which also allows so-called material basis decomposition, by which different materials and/or components in the examined subject or object can be identified and quantified, to be implemented effectively. Thirdly, more than two basis materials can be used which benefits decomposition techniques, such as K-edge imaging whereby distribution of contrast agents, e.g. iodine or gadolinium, are quantitatively determined. Fourth, there is no detector afterglow, meaning that high angular resolution can be obtained. Last but not least, higher spatial resolution can be achieved by using smaller pixel size.

A problem in any counting x-ray photon detector is the so-called pile-up problem. When the flux rate of x-ray photons is high there may be problems in distinguishing between two subsequent charge pulses. As mentioned above, the pulse length after the filter depends on the shaping time. If this pulse length is larger than the time between two x-ray photon induced charge pulses, the pulses will grow together and the two photons are not distinguishable and may be counted as one pulse. This is called pile-up. One way to avoid pile-up at high photon flux is thus to use a small shaping time, or to use depth-segmentation as suggested in optional embodiments described herein.

In order to increase the absorption efficiency, the detector can accordingly be arranged edge-on, in which case the absorption depth can be chosen to any length and the detector can still be fully depleted without going to very high voltages.

In particular, silicon has many advantages as detector material such as high purity and a low energy required for creation of charge carriers (electron-hole pairs) and also a high mobility for these charge carriers which means it will work even for high rates of x-rays.

The semiconductor x-ray detector sub-modules are normally tiled together to form a full detector of almost arbitrary size with almost perfect geometrical efficiency except for an optional anti-scatter module which may be integrated between at least some of the semiconductor detector modules.

More information on so-called photon-counting edge-on x-ray detectors in general can be found, e.g. in [4], which discloses an example of a photon-counting edge-on x-ray detector. In reference [4], there are multiple semiconductor detector modules arranged together to form an overall detector area, where each semiconductor detector module comprises an x-ray sensor oriented edge-on to incoming x-rays and connected to integrated circuitry for registration of x-rays interacting in the x-ray sensor.

As discussed, an overall x-ray detector may for example be based on detector sub-modules, or wafers, each of which has a number of depth segments in the direction of the incoming x-rays.

Such detector sub-modules can then be arranged or stacked one after the other and/or arranged side-by-side in a variety of configurations to form any effective detector area or volume. For example, a full detector for CT applications typically has a total area greater than 200 cm$^2$, which results in a large number of detector modules, such as 1500-2000 detector modules.

By way of example, detector sub-modules may generally be arranged side-by-side and/or stacked, e.g. in a planar or slightly curved overall configuration.

In general, it is desirable that incoming x-rays have the chance to pass through as many detector elements or segments as possible to provide as much spatial/energy information as possible.

Figure 5:
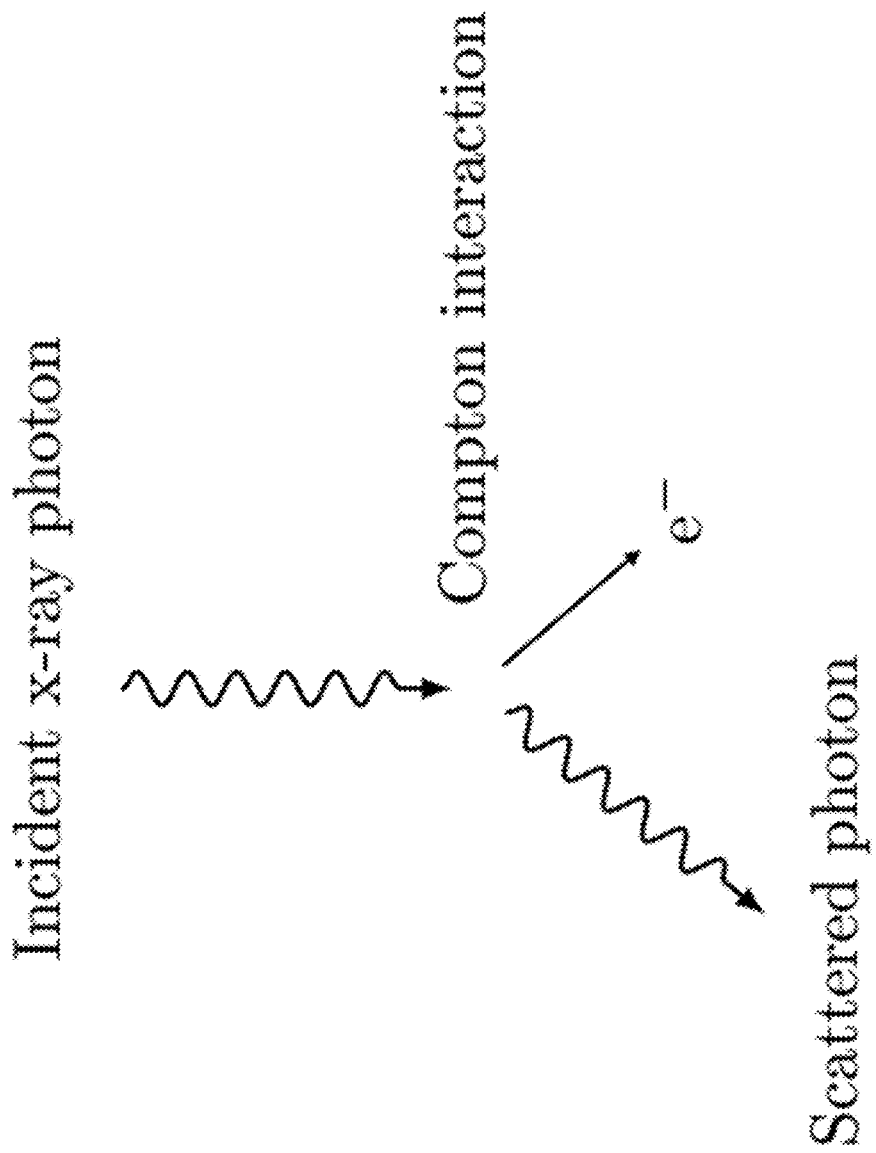
FIG. 5 is a schematic diagram illustrating the Compton effect.

Since the x-ray interactions will be distributed and occurring in different depth segments along the depth (length) of the sensor, the overall count rate will be distributed among the segments in depth, e.g. as can be seen from FIG. 5, which is a schematic diagram illustrating an example of the count rate in each segment. In this example, the first segment is the segment closest to the x-ray source.

By way of example, over a 40 mm deep sensor it would be possible to have 400 segments or more and the count rate would be correspondingly decreased. The sensor depth is vital for dose efficiency and the segmentation protects from pulse pile-up and maintains the spatial resolution of the system.

Figure 9:
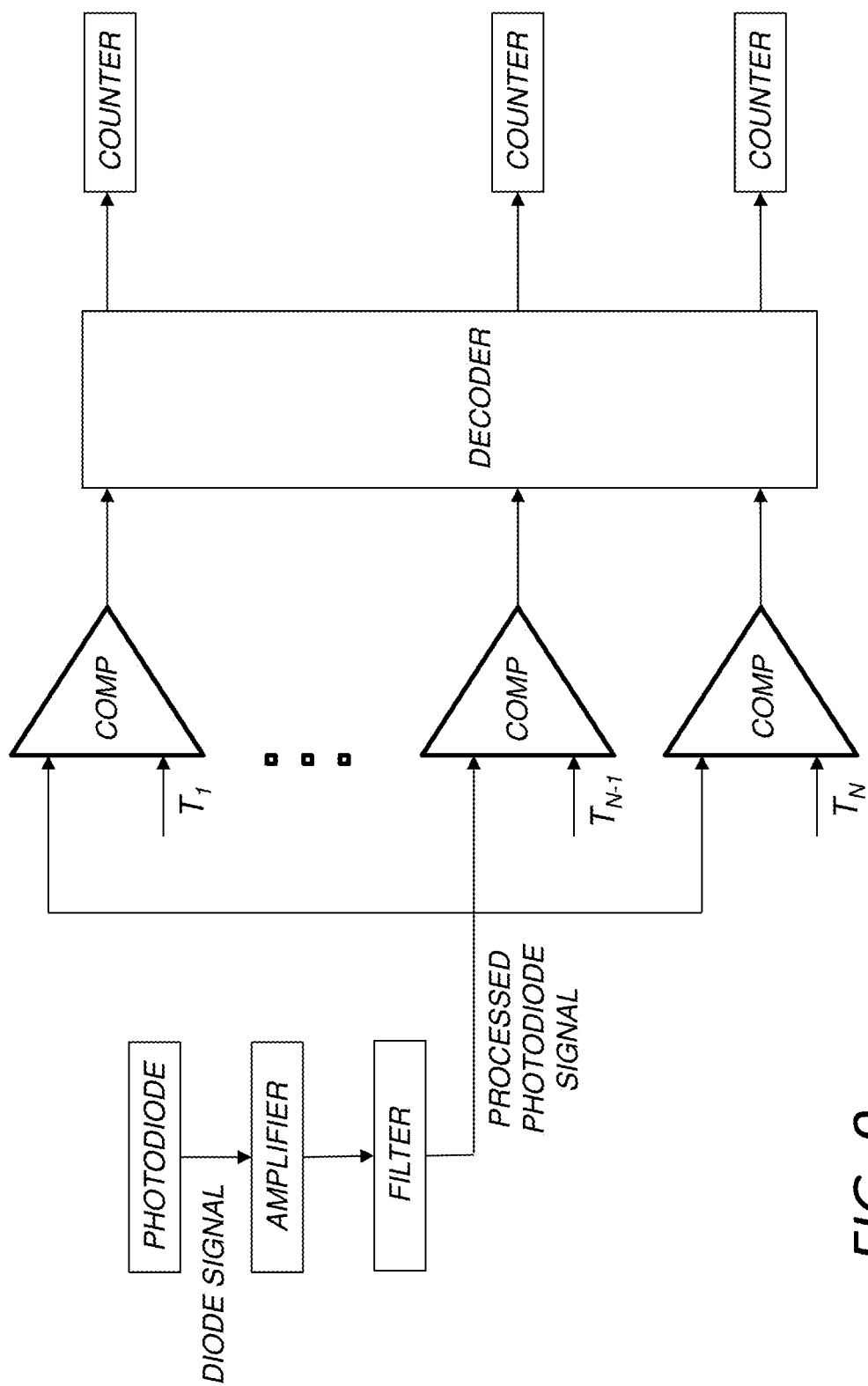
FIG. 9 is a schematic diagram illustrating an example of the conceptual structure for implementing an energy-discriminating photon-counting detector.

By way of example, the current may be measured, e.g., through a Charge Sensitive Amplifier (CSA), followed by a Shaping Filter (SF), e.g. as schematically illustrated in FIG. 9.

As the number of electrons and holes from one x-ray event is proportional to the x-ray energy, the total charge in one induced current pulse is proportional to this energy. The current pulse is amplified in the CSA and then filtered by the SF filter. By choosing an appropriate shaping time of the SF filter, the pulse amplitude after filtering is proportional to the total charge in the current pulse, and therefore proportional to the x-ray energy. Following the SF filter, the pulse amplitude may be measured by comparing its value with one or several threshold values ($T_1$-$T_N$) in one or more comparators (COMP), and counters are introduced by which the number of cases when a pulse is larger than the threshold value may be recorded. In this way it is possible to count and/or record the number of x-ray photons with an energy exceeding an energy corresponding to respective threshold value ($T_1$-$T_N$) which has been detected within a certain time frame.

When using several different threshold values, a so-called energy-discriminating photon-counting detector is obtained, in which the detected photons can be sorted into energy bins corresponding to the various threshold values. Sometimes, this particular type of photon-counting detector is also referred to as a multi-bin detector.

In general, the energy information allows for new kinds of images to be created, where new information is available and image artifacts inherent to conventional technology can be removed.

In other words, for an energy-discriminating photon-counting detector, the pulse heights are compared to a number of programmable thresholds ($T_1$-$T_N$) in the comparators and classified according to pulse-height, which in turn is proportional to energy.

However, an inherent problem in any charge sensitive amplifier is that it will add electronic noise to the detected current. In order to avoid detecting noise instead of real X-ray photons, it is therefore important to set the lowest threshold value high enough so that the number of times the noise value exceeds the threshold value is low enough not to disturb the detection of X-ray photons.

By setting the lowest threshold above the noise floor, electronic noise, which is the major obstacle in the reduction of radiation dose of the X-ray imaging systems, can be significantly reduced The shaping filter has the general property that large values of the shaping time will lead to a long pulse caused by the x-ray photon and reduce the noise amplitude after the filter. Small values of the shaping time will lead to a short pulse and a larger noise amplitude. Therefore, in order to count as many X-ray photons as possible, a large shaping time is desired to minimize noise and allowing the use of a relatively small threshold level.

The values of the set or table of thresholds, by which the pulse heights are compared in the comparators, affect the quality of the image data generated by the photon-counting detector. Furthermore, these threshold values are temperature dependent. Therefore, in an embodiment, the calibration data generated by the power-consuming circuitries is a set or table or thresholds ($T_1$-$T_N$).

It should though be understood that it is not necessary to have an energy-discriminating photon-counting detector, although this comes with certain advantages.

Figure 3D:
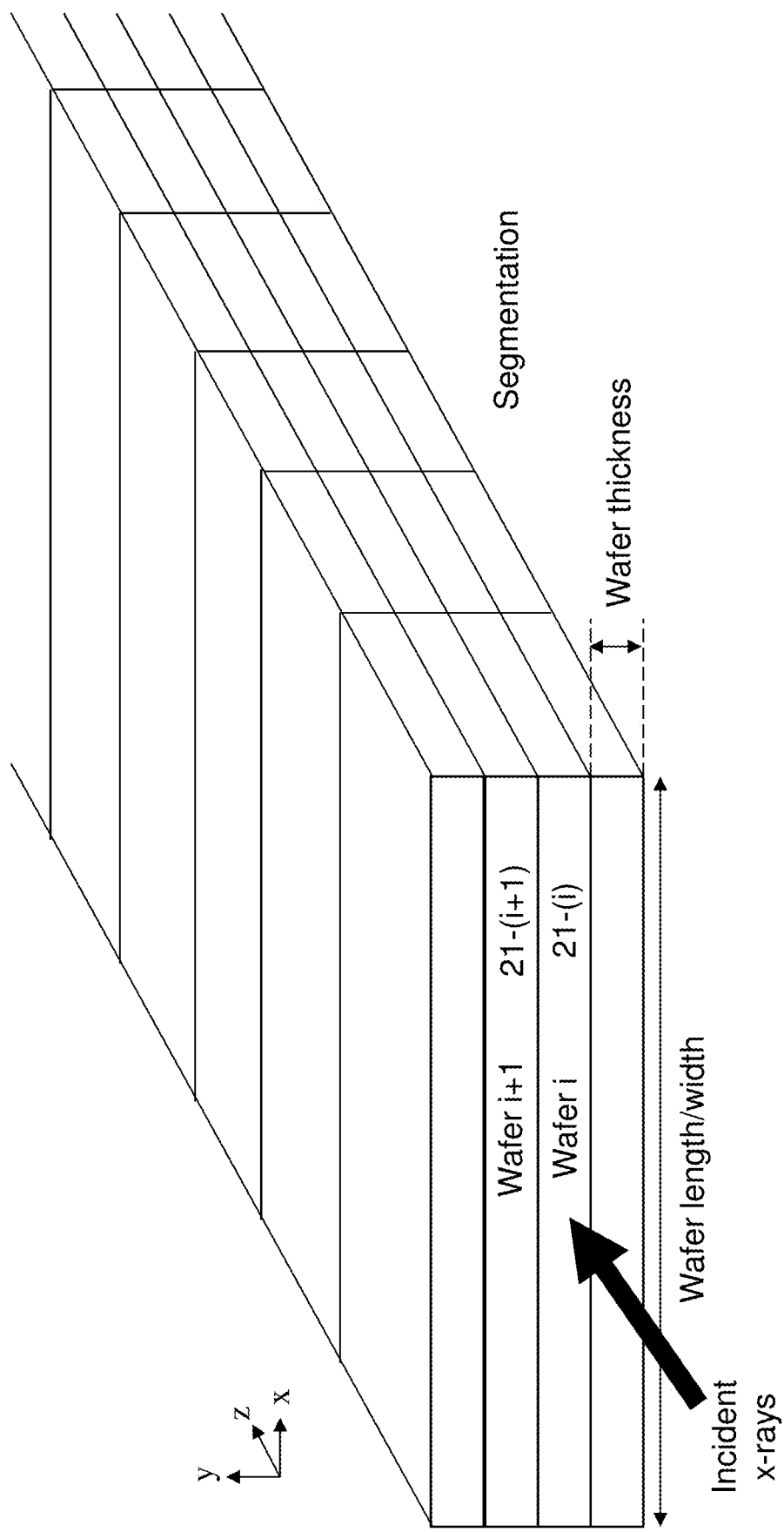
FIG. 3D is a schematic diagram illustrating an example of a photon-counting x-ray detector, which is based on a number of x-ray detector sub-modules, here referred to as wafers that are stacked one after the other.

FIG. 3D is a schematic diagram illustrating an example of a photon-counting x-ray detector, which is based on a number of x-ray detector sub-modules 21, here referred to as wafers. The wafers are stacked one after the other. It can be seen that each wafer has a length (x) and a thickness (y), and that each wafer is also segmented in the depth direction (z), so-called depth segmentation. Purely as an example, the length of the wafer may be in order of 25-50 mm, and the depth of the wafer may be in the same order of 25-50 mm, whereas the thickness of the wafer may be in the order of 300-900 um.

By way of example, each wafer 21 has detector elements distributed over the wafer in two directions including the direction of the incoming x-rays (z). Each wafer 21 has a thickness (y) with two opposite sides, such as a front side and a back side, of different potentials to enable charge drift towards the front side, where the detector elements, also referred to as pixels, are normally arranged.

For a better understanding of the proposed technology it may be useful to recall the basic concept of the Compton effect.

The incoming X-ray photons may interact with the semiconductor material of the detector modules either through the photoelectric effect, simply referred to as the photoeffect herein, or Compton interaction, see FIG. 5. Compton interaction, also referred to as Compton scattering, is the scattering of a photon by a charged particle, usually an electron. It results in a decrease in energy of the photon, called the Compton effect. Part of the energy of the photon is transferred to the recoiling electron. The photon may be involved in multiple Compton interactions during its path through the semiconductor substrate. Briefly, in a Compton interaction, an incident x-ray photon is deflected from its original path by an interaction with an electron, which is ejected from its initial orbital position to form a so-called secondary or "free" electron. Such a secondary electron can also be the result of the photoeffect, in which case the entire energy of the incident x-ray photon is transferred to the electron.

More specifically, an x-ray photon may create a secondary electron through Compton interaction or photoeffect. The electron will get kinetic energy from the x-ray photon and move a short distance, e.g. 1 um-50 um, and during its path will excite electron-hole pairs. Every electron hole pair will cost about 3.6 eV to create which means that for example a Compton interaction with 15 keV deposited energy to the electron will create around 4200 electron-hole pairs, forming a so-called charge cloud. The cloud will move or drift according to the electric field lines and if the backside of the detector sub-module or wafer is biased positive the holes will move towards the readout electrodes arranged on the front side of the detector sub-module or wafer and the electrons will move towards the back side. During drift, the electron-hole pairs forming the charge cloud will also be subject to diffusion, which basically means that the charge cloud will increase in size.

The readout electrodes are functioning as detector elements or pixels. By way of example, the voltage on the back side may be around 200 V and virtual ground on the front side.

As should be understood, it is proposed to orient the x-ray detector edge-on relative to the beam (i.e. edge-on relative to the incoming x-rays), while sub-dividing the sensor area into a relatively high resolution, e.g. into 5 um to 100 um resolution, in order to be able to resolve a charge cloud.

Figure 6A:
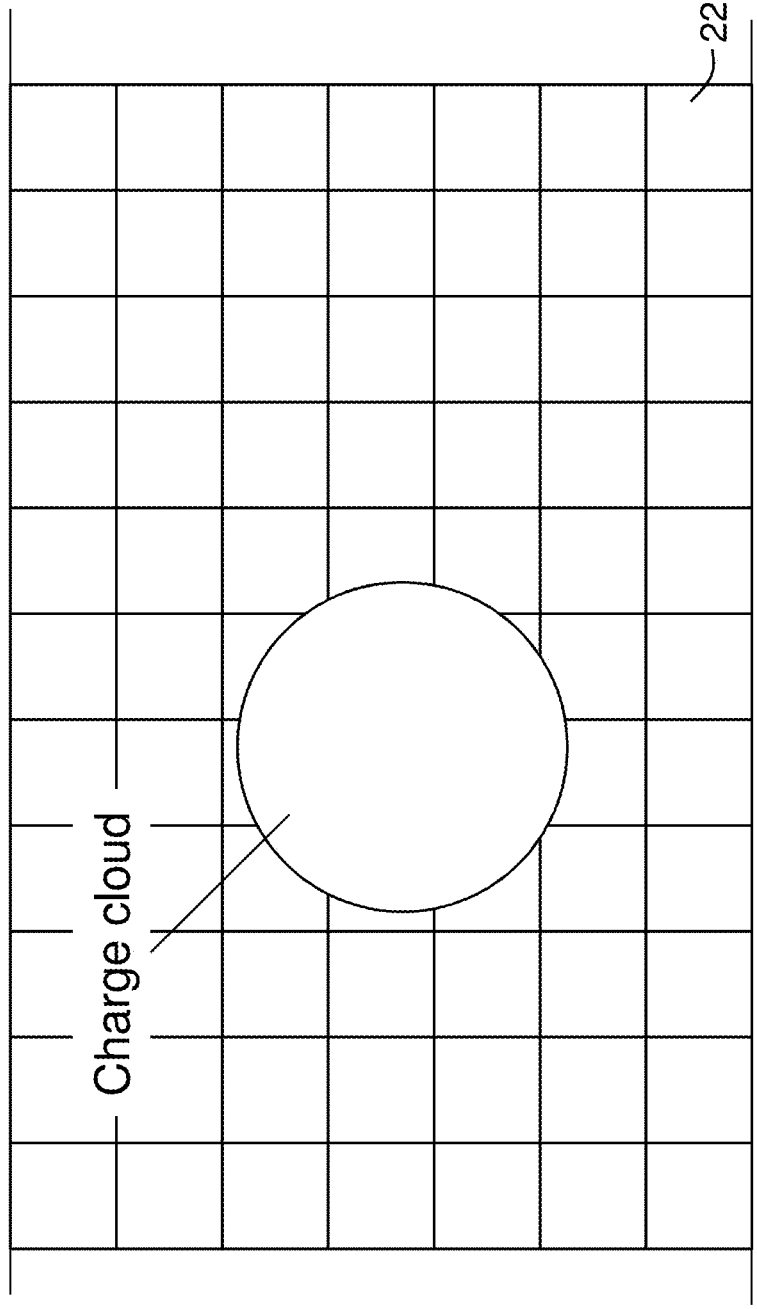
FIG. 6A is a schematic diagram illustrating an example of pixels of a particular wafer in the x-z plane.

FIG. 6A is a schematic diagram illustrating an example of the pixels of a particular wafer in the x-z plane. In this example, the pixels 22 (or at least a portion thereof) are generally smaller than the charge cloud to be resolved. For example, the charge cloud may have a width in the order of 100 um, and the pixels 22 are therefore normally designed to be smaller or even considerably smaller than that. Hence, an x-ray photon traveling through the semiconductor substrate typically results in a charge cloud covering multiple neighboring pixels in the detector module. This means that a single x-ray photon will most likely trigger event detection in multiple pixels.

In other words, the charge diffusion may be represented by a charge cloud, and in a particular example, at least a portion of the pixels 22, or detector elements, has a size that is smaller than the charge cloud.

Although the pixels are illustrated as squares, it should be understood that the pixels may be rectangular or have other forms.

According to a particular aspect, information about the charge diffusion may be used for providing improved resolution in at least one of the two directions over which the detector elements are distributed on the front side of the detector sub-module or wafer.

For example, increased resolution may be obtained based on information of a charge cloud profile in one or both of these directions. The considered direction(s) may include the length (x) direction and/or depth (z) direction of the detector sub-module or wafer.

Figure 6B:
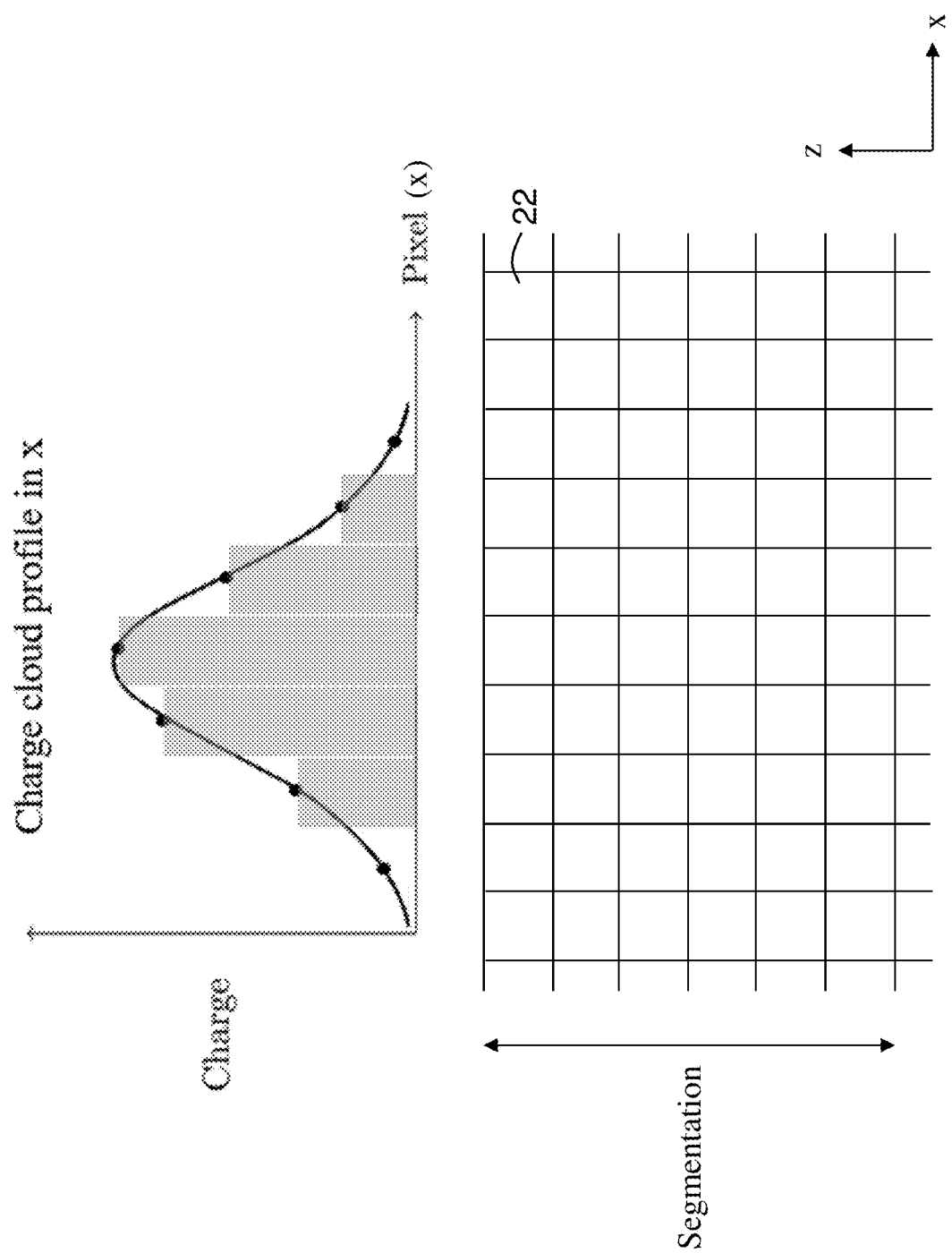
FIG. 6B is a schematic diagram illustrating an example of a charge cloud profile in the x-direction for a charge cloud.

FIG. 6B is a schematic diagram illustrating an example of a charge cloud profile in the x-direction for a charge cloud.

Figure 6C:
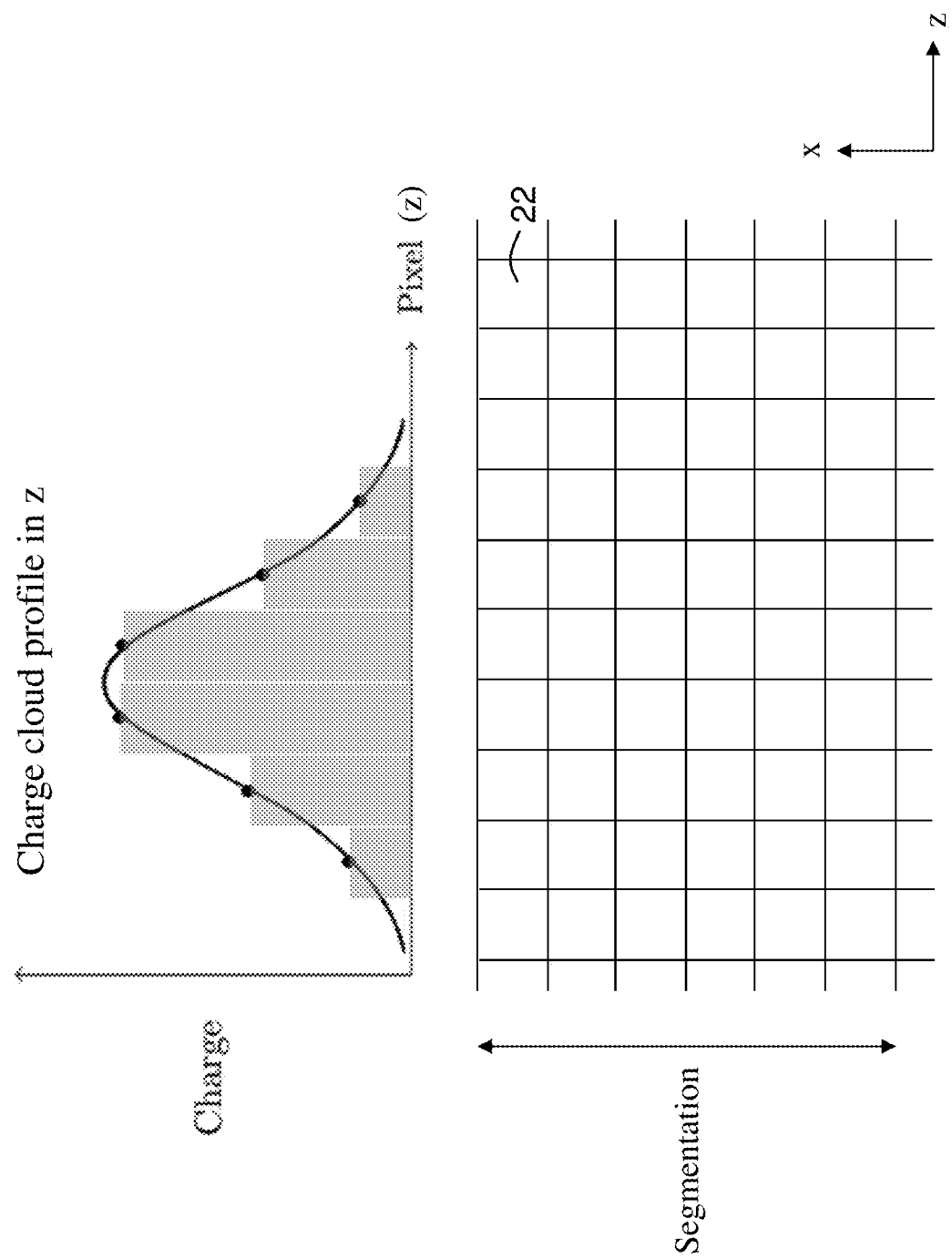
FIG. 6C is a schematic diagram illustrating an example of a charge cloud profile in the z-direction for a charge cloud.

FIG. 6C is a schematic diagram illustrating an example of a charge cloud profile in the z-direction for a charge cloud.

This may involve determining one or more charge cloud profiles (e.g. see FIG. 6B and FIG. 6C) and performing curve fitting through any standard curve fitting methods such as weighted averaging and/or least mean square methods. For example, finding out where the curve has its peak and identifying the peak as the point of interaction in a particular direction, can improve the resolution considerably, even down to sub-pixel resolution, e.g. down to 1 um resolution. This can be compared to the spatial resolution of conventional x-ray imaging systems, which may have a resolution of approximately 1 mm.

Alternatively, it may be possible to use information on which pixel 22 that has detected the highest charge as the point of interaction. It should though be understood that with a proper curve fitting, as described above, it may be possible to obtain sub-pixel resolution.

The inventors have also realized that the point of detection of a photon may differ quite significantly from the initial point of interaction, along the thickness (y) of the detector sub-module or wafer.

Figure 6D:
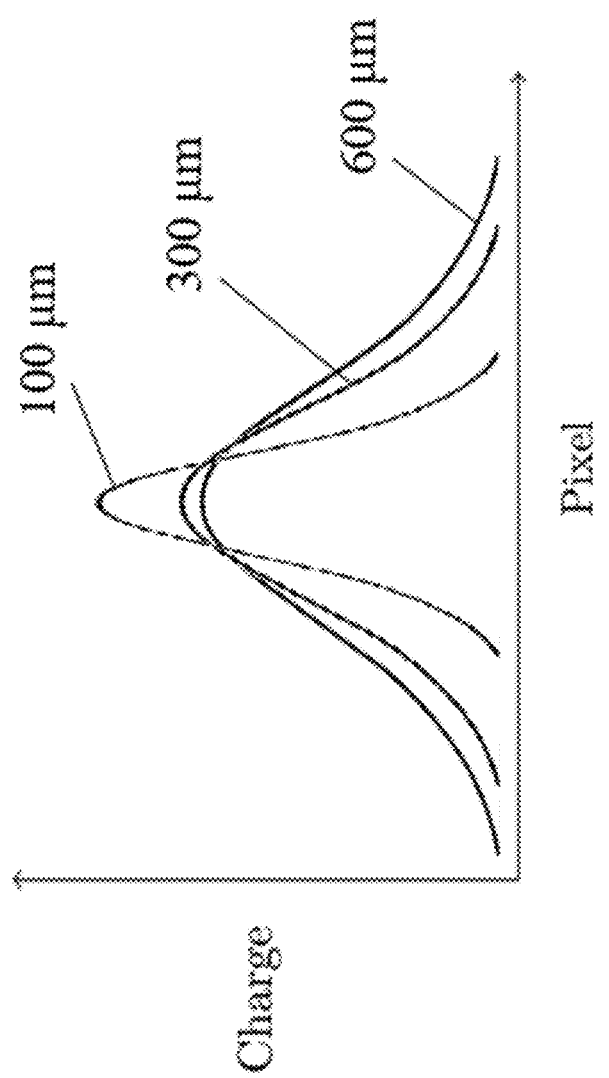
FIG. 6D is a schematic diagram illustrating an example of how the width of the charge diffusion or cloud is dependent on the distance, along the thickness of the considered detector sub-module or wafer of an x-ray detector, from the initial point of interaction to the point of detection.

After careful analysis and experiments, the inventors have further recognized that the shape, and in particular, the width of the charge diffusion or cloud is dependent on the distance, along the thickness of the considered detector sub-module or wafer of an x-ray detector, from the initial point of interaction to the point of detection. This is schematically shown in FIG. 6D for three different distances or depths (100 μm, 300 μm and 600 μm).

By way of example, if the charge cloud is not circular in cross-section but rather elliptical or of other forms, and thereby has different extensions in the different directions in the z-x plane, it is recommendable to use the smallest width of the charge cloud cross-section as a relevant measure of the charge diffusion.

During the movement of the charge cloud the charges will diffuse and this is accelerated by electrostatic repulsion. The induced current is dominated by movement of charge that occurs close to the front side. Since the diffusion is a function of time, the charge cloud will be wider (upon collection at the front side) if the interaction took place close to the back side (longer time) compared to close to the front side (negligible diffusion for contributing charge carriers). Knowing the total energy (integrated charge of the electron cloud) and the width of the cloud will enable an estimation of the point of interaction along the thickness of the edge-on wafer.

The area of the photon-counting detector, in which coincidental or near simultaneous events are detected in neighboring detector elements (in the x-y plane), thereby also gives depth information (in the z-direction) indicating the point of interaction between an incident x-ray photon and the semiconductor material. Thus, the larger the area of detection the wider the charge diffusion, implying a more remote point of interaction (such as 600 μm) as compared to the case with a smaller area of detection and narrow charge diffusion (such as 100 μm), as schematically illustrated in FIG. 6D. Experiments have shown that the resolution may be considerably improved, e.g. down to 50 um. This is a considerable improvement compared to simply knowing in which wafer the interaction took place. It is now also possible to know, within a resolution of approximately 50 um, where along the thickness of the wafer the initial point of interaction occurred.

It may thus be desirable to enable improved estimation of an initial point of interaction of an x-ray photon in a photon-counting x-ray detector, which is based on a number of x-ray detector sub-modules or wafers, each of which comprises detector elements distributed over the detector sub-module or wafer in two directions including the direction of the incoming x-rays.

Each detector sub-module or wafer has a thickness with two opposite sides, such as a front side and a back side, of different potentials to enable charge drift towards the front side, where the detector elements, also referred to as pixels, are arranged.

It is possible to determine an estimate of charge diffusion originating from a Compton interaction or possibly from an interaction through photoeffect related to the x-ray photon in an x-ray detector sub-module or wafer of the x-ray detector, and estimate the initial point of interaction along the thickness of the detector sub-module based at least partly on the determined estimate of charge diffusion.

By way of example, it may be possible to determine an estimate of a distance, along the thickness of the detector sub-module, between the point of detection of the x-ray photon in the detector sub-module and the initial point of interaction based on the estimate of charge diffusion, and then determine an estimate of the initial point of interaction based on the point of detection and the determined estimate of a distance along the thickness of the detector sub-module.

The thickness of the detector sub-module or wafer generally extends in the drift direction between the back side and front side of the detector sub-module.

By way of example, the shape, and in particular, the width of the charge diffusion is measured or estimated, and the distance between the point of detection and the initial point of interaction is determined based on the shape or width of the charge diffusion or distribution.

For example, the detector elements distributed over the detector sub-module or wafer on the front side provide an array of pixels, where the pixels are generally smaller than the charge cloud to be resolved.

The two directions over which the detector elements are distributed on the front side of the considered detector sub-module or wafer typically include the length and depth directions of the detector sub-module. The direction of the incoming x-rays generally corresponds to the depth direction and this is the reason for calling this type of x-ray detector a depth-segmented x-ray detector or edge-on x-ray detector.

The proposed technology thus offers considerable improvements for x-ray imaging and/or image reconstruction, more specifically significantly increased resolution.

This means that for the first time we can enable phase shift imaging in clinical solutions and/or combine absorption imaging with phase contrast imaging in a detector that is practical for clinical use.

In the following, non-limiting examples of embodiments for providing x-ray detector sub-modules and pixels suitable for the proposed technology will be described.

It has been suggested to implement detector sub-modules, sometimes simply referred to as detector modules, as so-called Multi-Chip Modules (MCMs) in the sense that the detector modules have semiconductor base substrates for electric routing and for a number of ASICs. The routing will include a connection for the signal from each pixel to an ASIC input as well as connections from the ASICs to external memory and/or digital data processing. Power to the ASICs may be provided through similar routing taking into account the increase in cross-section which is required for the large currents in these connections, but the power may also be provided through a separate connection. Hence, each individual pixel is connected to a subsequent ASIC channel where an MCM technology is employed to integrate the ASICs and electric routing on the silicon substrate.

The proposed technology provides further improvements over prior art x-ray detectors, e.g. by using active integrated pixels in the detector modules. This means that part of the analog processing of the electric signals is moved from the ASICs into the pixels. For instance, moving the pre-amplifying from the ASICs to the pixels lower the capacitance at the input to the pre-amplifiers since no long traces are needed to route the signal from the pixels to the ASICs. Further advantages of integrating at least part of the analog signal processing in the pixels include smaller pixel sizes, which in turn reduces the power consumption per pixel and enables a reduction of the minimum noise threshold.

FIG. 7 is a schematic diagram of a detector module, also referred to as a wafer or chip, according to an embodiment. In this example, the detector module 21 comprises a semiconductor substrate or material comprising a plurality of active integrated pixels 22 arranged in the semiconductor substrate. In a particular embodiment, the plurality of active integrated pixels is arranged at a main side (front side) of the semiconductor substrate in a grid or matrix, or other pattern, as shown in the figure. The figure also illustrates the arrangement of the pixels in different depth segments with regard to the edge facing the X-ray source and at which X-rays incident on the detector module.

In an embodiment, the detector module 21 also comprises further processing circuitry, such as analog processing circuitry and/or digital processing circuitry, exemplified as read-out circuitry, control circuitry and analog-to-digital conversion (ADC) circuitry in the figure. This further processing circuitry may be implemented in or as one or more ASICs.

The further processing circuitry is advantageously arranged in the semiconductor substrate at the same main side (front side) as the plurality of active integrated pixels. In such a case, the further processing circuitry is preferably arranged at the portion or part of the main side at or in connection with the edge facing away from the X-ray source and the incident x-ray as shown in the figure. This embodiment reduces any dead area of the detector module by reducing the portion of the detector module that is used for the further processing circuitry. In addition, the further processing circuitry is protected from the incoming X-ray by be arranged furthest away from the edge of incidence.

In an illustrative, but non-limiting, example the area of the semiconductor substrate comprising active integrated pixels may be from 5×5 mm up to 50×50 mm, such as 10×10 mm, 15×15 mm, 20×20 mm, 25×25 mm, 30×30 mm, 35×35 mm, 40×40 mm or 45×45 mm. Also, non-quadratic, such as rectangular, areas with active integrated pixels are possible.

In FIG. 3D, each wafer may comprise one detector module or may comprise multiple detector modules. In the latter case, the detector modules may be attached to a thin substrate, such as a ceramic substrate, to form a wafer that can be handled as a single unit. Sometime, this single unit may itself be referred to as a detector module, or a detector sub-module. Purely as an example, the width of the wafer may be in order of 25-50 mm, and the depth of the wafer may be in the same order of 25-50 mm, whereas the thickness of the wafer may be in the order of 300-900 µm.

FIG. 7 schematically also indicates an active integrated pixel with a so-called detector diode (electrode) together with read-out electronics and interconnections. Each such active integrated pixel typically has a size in the μm range. In an embodiment, the active integrated pixels are quadratic and typically all active integrated pixels in a detector module have the same shape and size. It is, however, possible to use other shapes for the pixels 22, such as rectangular, and/or having active integrated pixels with different sizes and/or shapes in the same detector module as shown in FIG. 8. In FIG. 8, the active integrated pixels 22 have the same width but different depths. For instance, the depth of the active integrated pixels may increase for different depth segment and thereby based on the distance to the edge at which the X-rays incident on the detector module. This means that the active integrated pixels at this edge preferably have smaller depth as compared to active integrated pixels closest to the opposite edge. In such an embodiment, the detector modules may include active integrated pixels having two or more different depths.

Different pixel depths, and in particular pixel depth as a function of depth segment or distance to the edge at which the X-rays incident on the detector module can be used to tailor the probabilities or likelihoods for detecting an event at an active integrated pixel.

According to a specific aspect of the proposed technology, all or part of the analog signal processing illustrated in FIG. 9 may be integrated into the pixels to thereby form so-called active integrated pixels.

As mentioned, an aspect of the invention relates to an edge-on photon-counting detector. The edge-on photon-counting detector comprises at least one detector module having a respective edge facing incident X-rays. Said at least one detector module comprises a semiconductor substrate.

In a particular example, the edge-on photon-counting detector also comprises a plurality of active integrated pixels arranged in the semiconductor substrate.

In an embodiment, the edge-on photon-counting detector comprises multiple detector modules arranged side-by-side and/or stacked.

The edge-on photon-counting detector is typically fabricated based on silicon as semiconductor material for the detector modules.

To compensate for the low stopping power of silicon, the detector modules are typically oriented in edge-on geometry with their edge directed towards the X-ray source, thereby increasing the absorption thickness. In order to cope with the high photon fluxes in clinical CT, a segmented structure of the active integrated pixels into depth segments is preferably applied, which is achieved by implanting individual active integrated pixels in depth segments on the silicon substrate.

In a particular embodiment, the semiconductor substrate is made of float zone (FZ) silicon. FZ silicon is very pure silicon obtained by vertical zone melting. In the vertical configuration molten silicon has sufficient surface tension to keep the charge from separating. Avoidance of the necessity of a containment vessel prevents contamination of the silicon. Hence, the concentrations of light impurities in the FZ silicon are extremely low. The diameters of FZ silicon wafers are generally not greater than 200 mm due to the surface tension limitations during growth. A polycrystalline rod of ultra-pure electronic grade silicon is passed through an RF heating coil, which creates a localized molten zone from which the crystal ingot grows. A seed crystal is used at one end in order to start the growth. The whole process is carried out in an evacuated chamber or in an inert gas purge. The molten zone carries the impurities away with it and, hence, reduces impurity concentration.

Specialized doping techniques like core doping, pill doping, gas doping and neutron transmutation doping may be used to incorporate a uniform concentration of impurity.

The semiconductor substrate is, in an embodiment, made of high resistivity silicon, such as high resistivity FZ silicon. As used herein, high resistivity silicon is defined as monocrystalline silicon having a bulk resistivity larger than 1 kΩcm.

The plurality of active integrated pixels may be implemented as active integrated Complementary Metal Oxide Semiconductor (CMOS) pixels in the semiconductor substrate. Hence, the analog circuitry of the active integrated pixels may be produced using CMOS technology.

FIGS. 10 to 13 illustrate various embodiments of such active integrated pixels with different analog read-out electronics in the pixels. In these figures, the current generating part of the pixel is illustrated as a diode outputting a current pulse or diode signal.

Figures 10, 11:
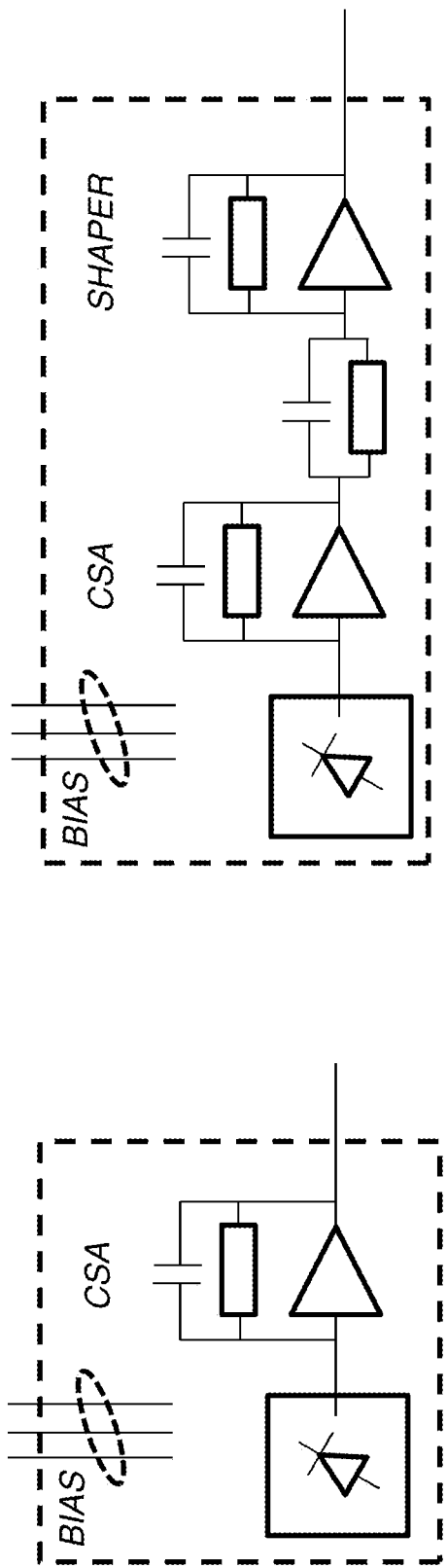
FIG. 10 is a schematic diagram illustrating an example of an active integrated pixel according to an embodiment.
FIG. 11 is a schematic diagram illustrating another example of an active integrated pixel according to another embodiment.

FIG. 10 illustrates an embodiment of an active integrated pixel comprising an amplifier configured to generate an output signal based on a current pulse generated by the active integrated pixel or diode. In an embodiment, the amplifier is a charge sensitive amplifier (CSA) configured to integrate the current pulse into a voltage signal.

The output signal, such as voltage signal, from the amplifier, preferably CSA, is in this embodiment routed to external processing circuitry arranged in the semiconductor substrate in the detector module, such as in the form of one or more ASICS, see read-out, ctrl and ADC in FIGS. 7 and 8.

With an increased number of active integrated pixels in the detector module the count rate per pixel decreases and also the noise requirements are relaxed. This implies that amplifiers with comparatively low power consumption and low bandwidth can be used in the active integrated pixels. Furthermore, single-ended amplifiers are preferred due to the nature of the diode. This further allows for less complex amplifiers. The lower diode capacitance, the input referred noise from the amplifier will be less dominant as compared to using larger pixel sizes.

FIG. 11 illustrates another embodiment of an active integrated pixel. This embodiment comprises a pulse shaper, also referred to as shaping filter, in addition to the amplifier. This pulse shaper is configured to filter the output signal from the amplifier.

The current pulse from the diode is preferably integrated using a CSA. Typically, this generates a slow-moving voltage at the output of the CSA. To compensate for this behavior a cancellation circuit (CC), such as a pole-zero cancellation circuit, is arranged connected to the CSA and the pulse shaper. This pole-zero CC cancels or at least suppresses the slow response of the CSA with maintained charge/current integration. Accordingly, the time constant will instead be determined by the shaper integration time of the pulse shaper.

The output signal from the pulse shaper is in this embodiment routed to external processing circuitry arranged in the semiconductor substrate in the detector module, such as in the form of one or more ASICS, see read-out, ctrl and ADC in FIGS. 7 and 8.

Figure 12:
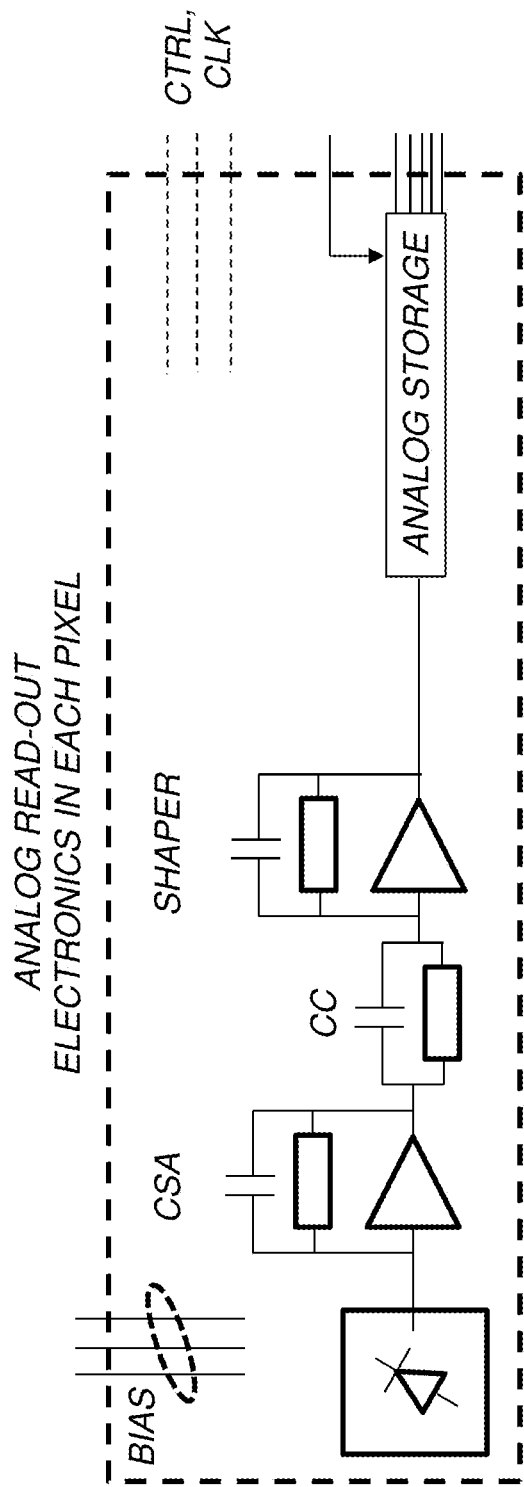
FIG. 12 is a schematic diagram illustrating yet another example of an active integrated pixel according to a further embodiment.

FIG. 12 illustrates a further embodiment of an active integrated pixel. This embodiment comprise an analog storage connected to, and arranged downstream of, the pulse shaper. This analog storage could be implemented in the active integrated pixel to at least temporarily store and retain the output signal from the pulse shaper. This enables controlled read-out of data from the active integrated pixel and the analog storage, such as based on a control signal (ctrl) and or at scheduled time instances, such as controlled based on a clock signal (clk).

An analog storage as shown in FIG. 12 may also be used in an embodiment as shown in FIG. 10, i.e., without any pulse shaper. In such a case, the analog storage is connected to the amplifier (CSA) or connected to the amplifier (CSA) through the pole-zero CC.

Figure 13:
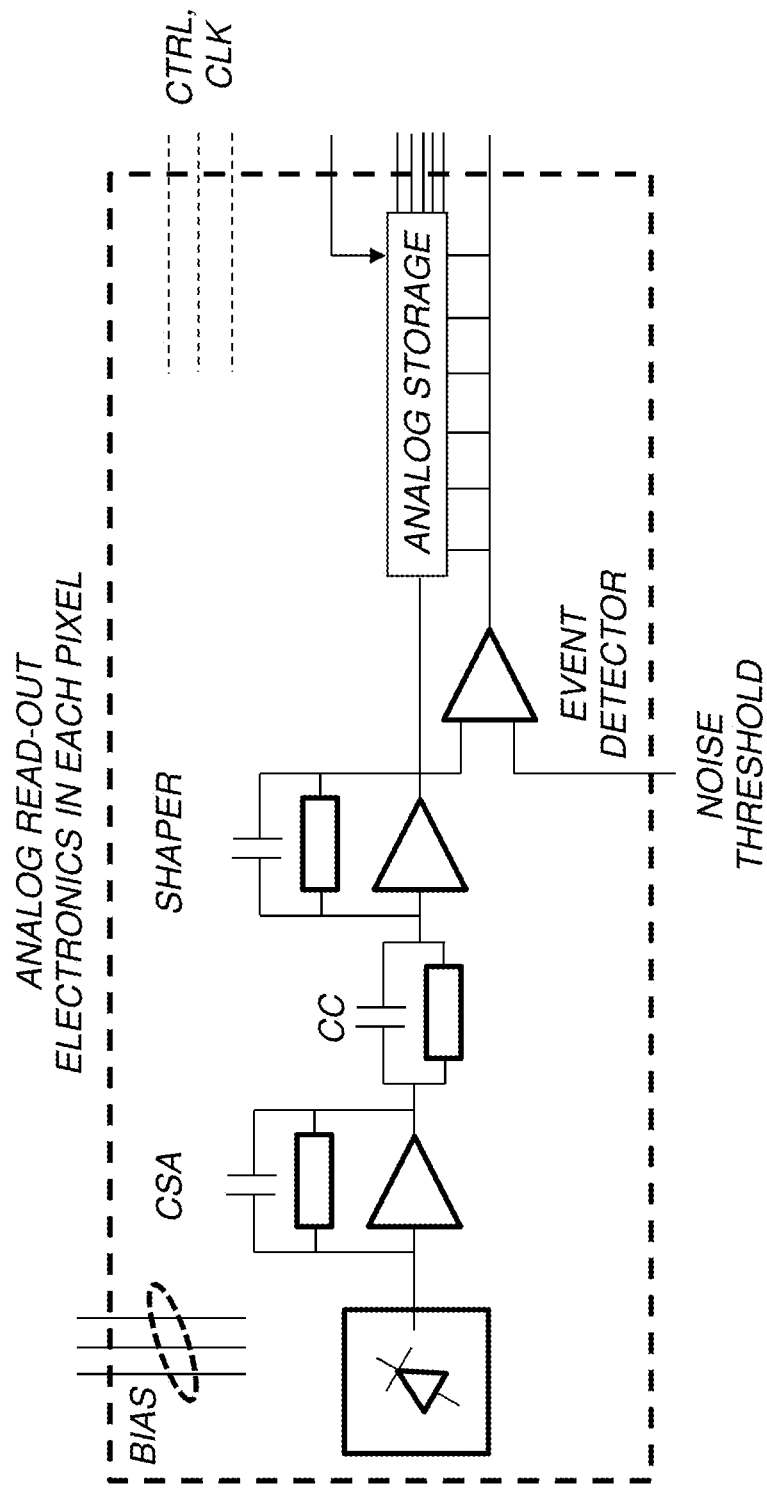
FIG. 13 is a schematic diagram illustrating still another example of an active integrated pixel according to yet another embodiment.

In yet another embodiment as shown in FIG. 13, the pixel comprises an event detector represented as a comparator in the figure. This event detector is then configured to detect a photon event by comparing a pulse amplitude of the output signal from the pulse shaper with a threshold value, represented by a noise threshold in the figure.

In a particular embodiment, the event detector is configured to generate a trigger signal based on the comparison of the pulse amplitude with the threshold value, and preferably generates the trigger signal if the pulse amplitude is equal to or exceeds, or exceeds, the threshold value.

In this embodiment, read-out of the analog storage may be controlled by the trigger signal output by the event detector. Thus, read-out of the data in the analog storage then takes place preferably only when the event detector confirms detection of a photon event by the active integrated pixel as represented by having a pulse amplitude (equal to or) above a noise floor as represented by the noise threshold.

In other words, a comparator acting as an event detector can be used to signal to read-out circuitry, typically arranged externally relative to the active integrated pixel, see read-out in FIGS. 7 and 8. This read-out circuitry reads the analog storage based on the trigger signal from the event detector. The read data may then be further processed, such as compared to thresholds ($T_1$-$T_N$), see FIG. 9, and/or digitized in an ADC, see FIGS. 7 and 8.

If no read-out of the data in the analog storage is performed the data therein may be consecutively flushed, such as by operating in a first-in-first-out (FIFO) manner. This allows for an asynchronous read out of the data from the analog storage and thereby a reduction in the power consumption during read out.

The trigger signal from the event detector may also be fed to neighboring active integrated pixels in the detector module to trigger them to store data that may then be read out and further processed. This enables detection of properties of the data even through the noise thresholding is not passed.

In another embodiment, read out of the analog storage is performed based on not only a trigger signal from the event detector in the active integrated pixel but also from a respective trigger signal from at least one neighboring active integrated pixel in the detector module.

By way of example, implementations of active integrated pixels enable a reduction in size of the pixels as compared to prior art solutions. This small size of the active integrated pixels allows multiple active integrated pixels in a detector sub-module to detect a charge cloud generated by a single x-ray photon. This in turn enables determination of an estimate of charge diffusion originating from a Compton interaction or an interaction through photoeffect related to the X-ray photon in a particular detector sub-module of the edge-on photon-counting detector, and estimation of the initial point of interaction of the x-ray photon along the thickness of the detector sub-module at least partly based on the determined estimate of charge diffusion, e.g. as previously described.

Figure 14:
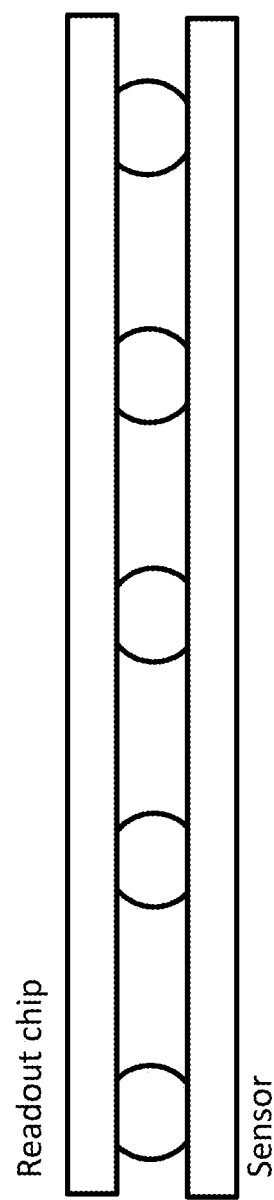
FIG. 14 is a schematic diagram illustrating an example of a bump-bonded chip.

FIG. 14 is a schematic diagram illustrating an example of a bump-bonded chip. The readout electronics will be integrated in the high resistivity detector silicon or the readout ASIC will be bump bonded to the sensor, as illustrated in FIG. 14.

Figure 15:
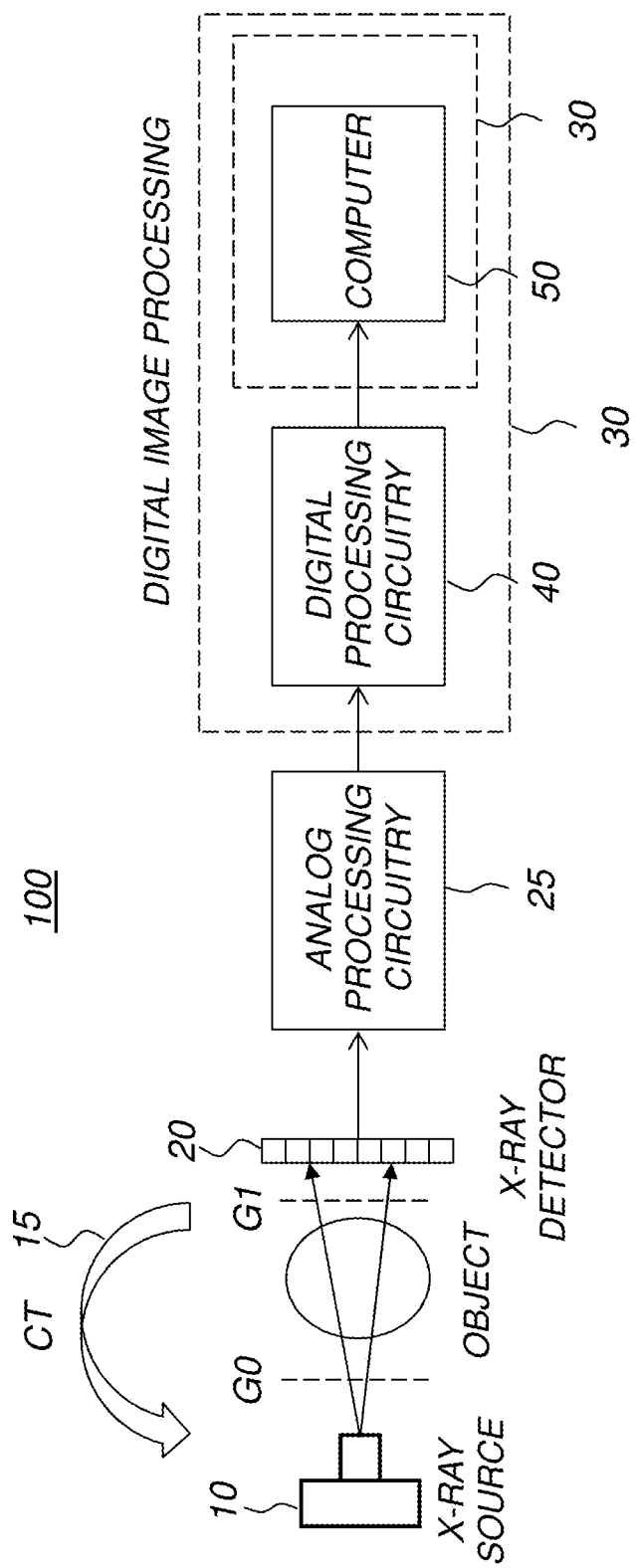
FIG. 15 is a schematic diagram illustrating another example of an x-ray imaging system.

FIG. 15 is a schematic diagram illustrating an example of an x-ray imaging system 100 comprises an x-ray source 10, which emits x-rays; an x-ray detector system 20, which detects the x-rays after they have passed through the object; analog processing circuitry 25, which processes the raw electrical signal from the detector and digitizes it; digital processing circuitry 40 which may carry out further processing operations on the measured data such as applying corrections, storing it temporarily, or filtering; and a computer 50 which stores the processed data and may perform further post-processing and/or image reconstruction. Optional gratings are also indicated, as previously discussed.

The overall detector may be regarded as the x-ray detector system 20, or the x-ray detector system 20 combined with the associated analog processing circuitry 25.

The digital part including the digital processing circuitry 40 and/or the computer 50 may be regarded as a digital image processing system 30, which performs image reconstruction based on the image data from the x-ray detector. The image processing system 30 may thus be seen as the computer 50, or alternatively the combined system of the digital processing circuitry 40 and the computer 50, or possibly the digital processing circuitry 40 by itself if the digital processing circuitry is further specialized also for image processing and/or reconstruction.

An example of a commonly used x-ray imaging system is a Computed Tomography (CT) system, which may include an x-ray source that produces a fan or cone beam of x-rays and an opposing x-ray detector system for registering the fraction of x-rays that are transmitted through a patient or object. The x-ray source and detector system are normally mounted in a gantry that rotates around the imaged object.

Accordingly, the x-ray source 10 and the x-ray detector system 20 illustrated in FIG. 15 may thus be arranged as part of a CT system, e.g. mountable in a CT gantry.

It will be appreciated that the methods and devices described herein can be combined and re-arranged in a variety of ways.

For example, specific functions may be implemented in hardware, or in software for execution by suitable processing circuitry, or a combination thereof.

The steps, functions, procedures, modules and/or blocks described herein may be implemented in hardware using any conventional technology, such as semiconductor technology, discrete circuit or integrated circuit technology, including both general-purpose electronic circuitry and application-specific circuitry.

Particular examples include one or more suitably configured digital signal processors and other known electronic circuits, e.g. discrete logic gates interconnected to perform a specialized function, or Application Specific Integrated Circuits (ASICs).

Alternatively, at least some of the steps, functions, procedures, modules and/or blocks described herein may be implemented in software such as a computer program for execution by suitable processing circuitry such as one or more processors or processing units.

Examples of processing circuitry includes, but is not limited to, one or more microprocessors, one or more Digital Signal Processors (DSPs), one or more Central Processing Units (CPUs), video acceleration hardware, and/or any suitable programmable logic circuitry such as one or more Field Programmable Gate Arrays (FPGAs), or one or more Programmable Logic Controllers (PLCs).

It should also be understood that it may be possible to re-use the general processing capabilities of any conventional device or unit in which the proposed technology is implemented. It may also be possible to re-use existing software, e.g. by reprogramming of the existing software or by adding new software components.

Figure 16:
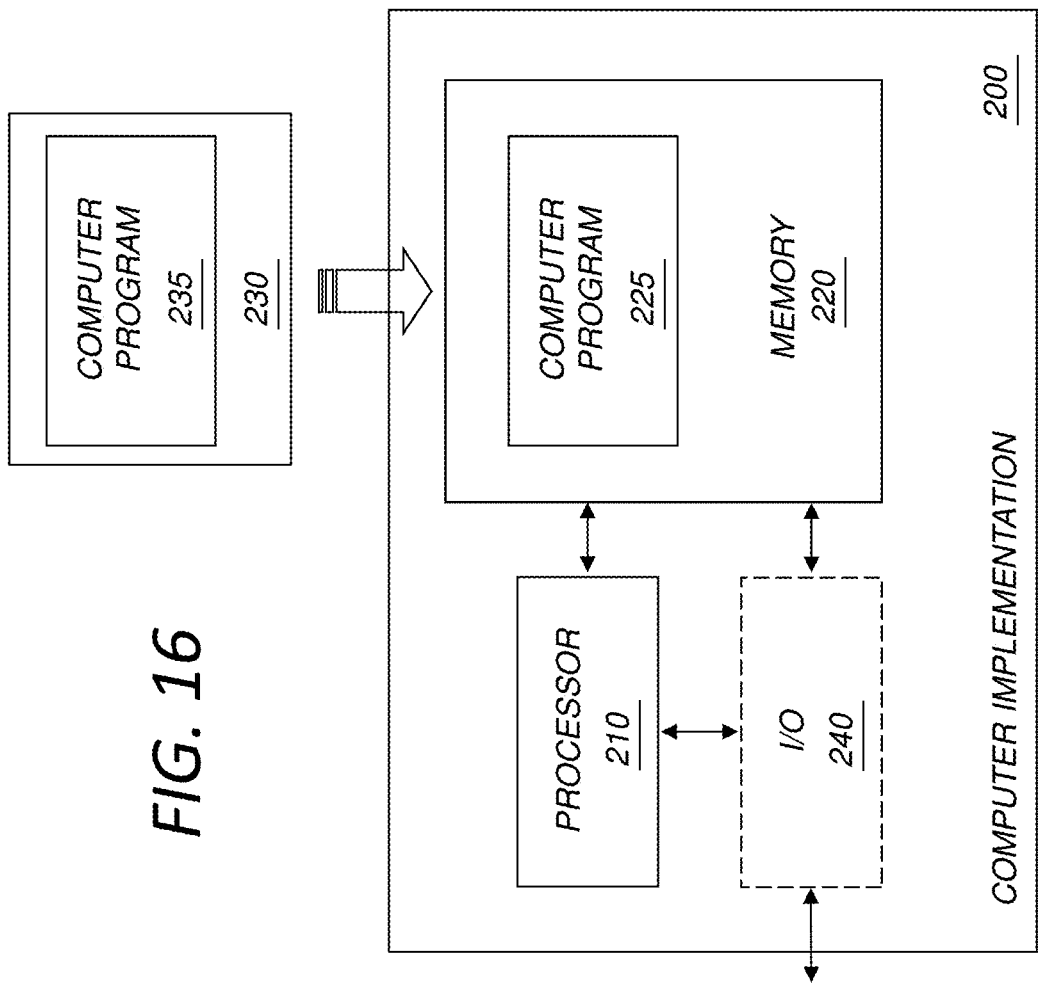
FIG. 16 is a schematic diagram illustrating an example of a computer implementation according to an embodiment.

FIG. 16 is a schematic diagram illustrating an example of a computer implementation according to an embodiment. In this particular example, the system 200 comprises a processor 210 and a memory 220, the memory comprising instructions executable by the processor, whereby the processor is operative to perform the steps and/or actions described herein. The instructions are typically organized as a computer program 225; 235, which may be preconfigured in the memory 220 or downloaded from an external memory device 230. Optionally, the system 200 comprises an input/output interface 240 that may be interconnected to the processor(s) 210 and/or the memory 220 to enable input and/or output of relevant data such as input parameter(s) and/or resulting output parameter(s).

By way of example, the x-ray imaging system comprises a processor and memory, the memory comprising instructions executable by the processor, whereby the processor is operative to determine an estimate or measure of charge diffusion and determine an estimate of a point of interaction of the incident x-ray photon based on the determined estimate or measure of charge diffusion.

The term 'processor' should be interpreted in a general sense as any system or device capable of executing program code or computer program instructions to perform a particular processing, determining or computing task.

The processing circuitry including one or more processors is thus configured to perform, when executing the computer program, well-defined processing tasks such as those described herein.

The processing circuitry does not have to be dedicated to only execute the above-described steps, functions, procedure and/or blocks, but may also execute other tasks.

The proposed technology also provides a computer-program product comprising a computer-readable medium 220; 230 having stored thereon such a computer program.

By way of example, the software or computer program 225; 235 may be realized as a computer program product, which is normally carried or stored on a computer-readable medium 220; 230, in particular a non-volatile medium. The computer-readable medium may include one or more removable or non-removable memory devices including, but not limited to a Read-Only Memory (ROM), a Random Access Memory (RAM), a Compact Disc (CD), a Digital Versatile Disc (DVD), a Blu-ray disc, a Universal Serial Bus (USB) memory, a Hard Disk Drive (HDD) storage device, a flash memory, a magnetic tape, or any other conventional memory device. The computer program may thus be loaded into the operating memory of a computer or equivalent processing device for execution by the processing circuitry thereof.

Method flows may be regarded as a computer action flows, when performed by one or more processors. A corresponding device, system and/or apparatus may be defined as a group of function modules, where each step performed by the processor corresponds to a function module. In this case, the function modules are implemented as a computer program running on the processor. Hence, the device, system and/or apparatus may alternatively be defined as a group of function modules, where the function modules are implemented as a computer program running on at least one processor.

The computer program residing in memory may thus be organized as appropriate function modules configured to perform, when executed by the processor, at least part of the steps and/or tasks described herein.

Alternatively, it is possibly to realize the modules predominantly by hardware modules, or alternatively by hardware. The extent of software versus hardware is purely implementation selection.

The embodiments described above are merely given as examples, and it should be understood that the proposed technology is not limited thereto. It will be understood by those skilled in the art that various modifications, combinations and changes may be made to the embodiments without departing from the present scope as defined by the appended claims. In particular, different part solutions in the different embodiments can be combined in other configurations, where technically possible.

REFERENCES

[1] Hard-X-ray dark-field imaging using a grating interferometer. Franz Pfeiffer et al., Nature Materials, Volume 7, pages 134-137 (2008).
[2] Takeda, Yoshihiro & Yashiro, Wataru & Suzuki, Yoshio & Momose, Atsushi. (2007). X-ray Phase Microtomography by Single Transmission Grating. AIP Conference Proceedings. 879. 10.1063/1.2436317.
[3] Warburton, W. (1997). An Approach to Sub-Pixel Spatial Resolution in Room Temperature X-Ray Detector Arrays with Good Energy Resolution. MRS Proceedings, 487, 531. doi:10.1557/PROC-487-531.
[4] U.S. Pat. No. 8,183,535.
[5] US 2013/0028379.
[6] WO 2014/100063.
[7] US 2017/0219503.
[8] US 2016/0324496.
[9] US 2014/0270070.
[10] CN 104569002.
[11] CN 105935297.

The invention claimed is:

1. An x-ray imaging system comprising an x-ray source, and an associated x-ray detector, wherein the x-ray detector is a photon counting x-ray detector for enabling detection of photon-counting events,
  wherein the x-ray imaging system is configured for enabling acquisition of at least one phase contrast image based on detected photon-counting events,
  wherein the x-ray detector is based on a number of x-ray detector sub-modules, also referred to as wafers, each of which comprises detector elements, wherein the x-ray detector sub-modules are oriented in edge-on geometry with their edge directed towards the x-ray source, assuming the x-rays enter through the edge,
  wherein each x-ray detector sub-module or wafer has a thickness with two opposite sides of different potentials to enable charge drift towards the side, where the detector elements, also referred to as pixels, are arranged, and
  wherein the x-ray imaging system is configured to determine an estimate or measure of charge diffusion originating from a Compton interaction or an interaction through photoeffect related to an incident x-ray photon in an x-ray detector sub-module or wafer of the x-ray detector, and to determine an estimate of a point of interaction of the incident x-ray photon in the x-ray detector sub-module based on the determined estimate or measure of charge diffusion.

2. The x-ray imaging system of claim 1, wherein the x-ray imaging system is configured for enabling acquisition of said at least one phase contrast image based at least partly on detected Compton events.

3. The x-ray imaging system of claim 1, wherein the x-ray imaging system further comprises a phase shift grating located between the object or subject to be imaged and the x-ray detector for enabling acquisition of said at least one phase contrast image.

4. The x-ray imaging system of claim 1, wherein the x-ray imaging system is configured to determine the estimate or measure of charge diffusion based on induced current caused by moving electron-hole pairs originating from the Compton interaction or interaction through photoeffect, as detected by detector elements distributed over the x-ray detector sub-module or wafer.

5. The x-ray imaging system of claim 1, wherein the x-ray imaging system is configured to determine, for each of a number of incident x-ray photons and/or each of a number of x-ray detector sub-modules, a corresponding estimate of charge diffusion originating from a Compton interaction or an interaction through photoeffect related to the incident x-ray photon in the x-ray detector sub-module, and to determine an estimate of the point of interaction of the incident x-ray photon in the respective x-ray detector sub-module.

6. The x-ray imaging system of claim 1, wherein each x-ray detector sub-module or wafer has detector elements distributed over the detector sub-module or wafer in two directions including i) the width/length direction (x) and ii) the depth direction (z) corresponding to the direction of the incoming x-rays, and
wherein the thickness (y) of the x-ray detector sub-module or wafer extends between the two opposite sides of the x-ray detector sub-module.

7. The x-ray imaging system of claim 1, wherein the x-ray imaging system is configured to determine, at least partly based on the determined estimate of charge diffusion, the estimate of the point of interaction of the incident x-ray photon in at least one of the three directions (x, y, z) of an x-ray detector sub-module or wafer.

8. The x-ray imaging system of claim 1, wherein the x-ray imaging system is configured to determine, at least partly based on the determined estimate of charge diffusion, the estimate of the point of interaction of the incident x-ray photon in at least one of the two directions (x, z) over which the detector elements are distributed on a main side of the x-ray detector sub-module or wafer, and/or along the thickness (y) of the x-ray detector sub-module.

9. The x-ray imaging system of claim 1, wherein the x-ray imaging system is configured to determine, at least partly based on the determined estimate of charge diffusion, the estimate of the point of interaction of the incident x-ray photon based on information of a charge cloud profile in one or both of the two directions (x, z) over which the detector elements are distributed on a main side of the x-ray detector sub-module or wafer.

10. The x-ray imaging system of claim 9, wherein the x-ray imaging system is configured for determining the charge cloud profile, performing curve fitting and finding out where the curve has its peak and identifying the peak as the point of interaction in a particular direction.

11. The x-ray imaging system of claim 1, wherein the x-ray imaging system is configured to determine the estimate of the point of interaction of the incident x-ray photon by identifying the pixel that has detected the highest charge as the point of interaction.

12. The x-ray imaging system of claim 1, wherein the x-ray imaging system is configured to estimate the initial point of interaction of the incident x-ray photon along the thickness (y) of the x-ray detector sub-module based at least partly on the determined estimate of charge diffusion.

13. The x-ray imaging system of claim 12, wherein the x-ray imaging system is configured to determine an estimate of a distance, along the thickness of the x-ray detector sub-module, between a point of detection of the x-ray photon in the x-ray detector sub-module and the initial point of interaction based on the estimate of charge diffusion, and determine the estimate of the initial point of interaction based on the point of detection and the determined estimate of a distance along the thickness of the detector sub-module.

14. The x-ray imaging system of claim 1, wherein the x-ray imaging system is configured to measure or estimate the shape and/or width of the charge diffusion.

15. The x-ray imaging system of claim 1, wherein the charge diffusion is represented by a charge cloud, and the x-ray imaging system is configured to estimate the initial point of interaction of the incident x-ray photon along the thickness (y) of the x-ray detector sub-module based on the measured width of the cloud and the integrated charge of the cloud.

16. The x-ray imaging system of claim 1, wherein the charge diffusion is represented by a charge cloud, and the detector elements distributed over the x-ray detector sub-module or wafer on a main side provide an array of pixels, where the pixels are smaller than the charge cloud to be resolved.

17. The x-ray imaging system of claim 1, wherein at least one of the x-ray detector sub-modules comprises a semiconductor substrate or material comprising a plurality of active integrated pixels arranged in the semiconductor substrate.

18. The x-ray imaging system of claim 17, wherein the x-ray detector sub-module allows multiple active integrated pixels in an x-ray detector sub-module to detect a charge cloud generated by a single x-ray photon.

19. The x-ray imaging system of claim 17, wherein all or part of the analog signal processing is integrated into the active integrated pixels.

20. The x-ray imaging system of claim 17, wherein the active integrated pixels are implemented as active integrated Complementary Metal Oxide Semiconductor (CMOS) pixels in the semiconductor substrate.

21. The x-ray imaging system of claim 1, wherein the x-ray imaging system is configured to simultaneously acquire at least one x-ray absorption image and at least one phase contrast image based on the detected events.

22. The x-ray imaging system of claim 1, wherein the x-ray imaging system is configured to combine information of both x-ray absorption and phase contrast images in an image reconstruction process.

23. The x-ray imaging system of claim 22, wherein the x-ray imaging system is configured to combine phase information as well as absorption information in the image reconstruction process to provide a merged image representation.

24. The x-ray imaging system of claim 1, wherein the x-ray imaging system is configured for G2-less phase contrast imaging, without using any analyzer absorption grating.

25. The x-ray imaging system of claim 1, wherein each x-ray detector sub-module has a number of depth segments of detector elements in the direction of the incoming x-rays.

26. The x-ray imaging system of claim 1, wherein the x-ray detector sub-modules are arranged one after the other and/or arranged side-by-side in a configuration to form an effective detector area or volume.

27. The x-ray imaging system of claim 1, wherein the x-ray imaging system further comprises an associated image processing device connected to the x-ray detector system for performing image processing and/or image reconstruction.

28. The x-ray imaging system of claim 1, wherein the x-ray imaging system is configured to enable phase contrast imaging for Computed Tomography.

29. The x-ray imaging system of claim 1, wherein the x-ray imaging system comprises a processor and memory, the memory comprising instructions executable by the processor, whereby the processor is operative to determine an estimate or measure of charge diffusion and determine an estimate of a point of interaction of the incident x-ray photon based on the determined estimate or measure of charge diffusion.

* * * * *